(12) United States Patent
Wu et al.

(10) Patent No.: US 8,962,331 B2
(45) Date of Patent: Feb. 24, 2015

(54) METHOD OF MAKING INDUCED PLURIPOTENT STEM CELL FROM ADIPOSE STEM CELLS USING MINICIRCLE DNA VECTORS

(75) Inventors: Joseph Wu, Palo Alto, CA (US); Michael T. Longaker, Stanford, CA (US); Mark A. Kay, Stanford, CA (US); Ning Sung, Stanford, CA (US); FangJun Jia, Stanford, CA (US); Zhi-Ying Chen, Shenzhen (CN); Nicholas Panetta, Pittsburg, PA (US); Deepak Gupta, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 430 days.

(21) Appl. No.: 12/931,476

(22) Filed: Feb. 1, 2011

(65) Prior Publication Data

US 2011/0244566 A1 Oct. 6, 2011

Related U.S. Application Data

(60) Provisional application No. 61/337,316, filed on Feb. 1, 2010.

(51) Int. Cl.
*C12N 15/00* (2006.01)
*C12N 5/00* (2006.01)

(52) U.S. Cl.
USPC .......................................... 435/455; 435/325

(58) Field of Classification Search
USPC .................................. 435/455, 325
See application file for complete search history.

(56) References Cited

U.S. PATENT DOCUMENTS 8,048,675 B1 * 11/2011 Irion .............................. 435/455
8,298,825 B1 * 10/2012 Hochedlinger et al. ....... 435/377

OTHER PUBLICATIONS

Moore (2002, DNA and Cell Biol., vol. 21(5/6), pp. 443-451).*
Thomson (1995, PNAS, vol. 92, pp. 7844-7848).*
Stem Cells: Scientific Progress and Future Research Directions, Department of Health and Human Services, Chapter 1, Jun. 2001.*
Stem Cells: Scientific Progress and Future Research Directions, Department of Health and Human Services, Chapter 3, Jun. 2001.*
Takahashi (Cell, 2006, vol. 126:663-676).*
Okita (Nature, Jul. 19, 2007, vol. 448, p. 313-317).*
Wernig (Nature, Jul. 19, 2007, vol. 448, p. 318-324).*
Yu (Science, Nov. 20, 2007, vol. 318, p. 1917-1920).*
Blelloch (Cell Stem Cell, Sep. 13, 2007, vol. 1, p. 245-247).*
Nakagawa (Nat Biotechnol, 2008, vol. 26: 101-106).*
Wernig (Cell Stem Cell, Jan. 2008, vol. 2: 10-12).*
Duinsbergen (Experimental Cell Res. Jul. 9, 2008, vol. 314, p. 3255-3263).*
Eminli (Stem Cells, Jul. 17, 2008, vol. 26, p. 2467-2474).*
Kim (Nature, Jul. 2008, vol. 454, No. 7204, p. 646-650, plus materials and method page).*
Aasen (Nature Biotech., Nov. 2008, vol. 26, No. 11, p. 1276-1284).*
Okita (Science, Nov. 7, 2008, vol. 322, p. 949-953).*
Loh (Blood, May 28, 2009, vol. 113, No. 22, p. 5476-5479).*
Kim (Cell, Feb. 6, 2009, vol. 136, p. 411-419).*
Kaji (Nature, Apr. 9, 2009, vol. 458, p. 771-776).*
Patel (Stem Cell Rev. Sep. 2010, vol. 6, No. 3, p. 367-380).*
Sun (PNAS, Sep. 15, 2009, vol. 106, No. 37, p. 15720-15725).*
Chen (Molecular Therapy, Sep. 2003, vol. 8, No. 3, p. 495-500).*
Chen (Human Gene Therapy, Jan. 2005, vol. 16, p. 126-131).*
Carey; et al., "Reprogramming of murine and human somatic cells using a single polycistronic vector", PNAS (2009), 106(1):157-162.
Chen; et al., "Improved Production and Purification of Minicircle DNA Vector Free of Plasmid Bacterial Sequences and Capable of Persistent Transgene Expression in Vivo", Human Gene Therapy (2005), 16:126-131.
Jia, et al., "A Nonviral Minicircle Vector for Deriving Human iPS Cells", Nature Methods (2010), 7(3):197-199.
Sun; et al., "Feeder-free derivation of induced pluripotent stem cells from adult human adipose stem cells", PNAS (2009), 106(37):15720-15725.

* cited by examiner

*Primary Examiner* — Michael C. Wilson
(74) *Attorney, Agent, or Firm* — Bozicevic, Field & Francis LLP; Kyle A. Gurley; Pamela J. Sherwood

(57) ABSTRACT

Human somatic cells are reprogrammed to become induced pluripotent stem cells (iPS cells) by the introduction of a minicircle DNA vector. Cells of interest include adipose stem cells.

6 Claims, 22 Drawing Sheets
(19 of 22 Drawing Sheet(s) Filed in Color)

METHOD OF MAKING INDUCED PLURIPOTENT STEM CELL FROM ADIPOSE STEM CELLS USING MINICIRCLE DNA VECTORS

FEDERALLY SPONSORED RESEARCH AND DEVELOPMENT

This invention was made with Government support under HL064274 and OD004437 awarded by the National Institutes of Health. The Government has certain rights in this invention.

BACKGROUND OF THE INVENTION

The generation of pluripotent stem cells that are genetically identical to an individual provides unique opportunities for basic research and for potential immunologically-compatible novel cell-based therapies. Methods to reprogram primate differentiated somatic cells to a pluripotent state include differentiated somatic cell nuclear transfer, differentiated somatic cell fusion with pluripotent stem cells and direct reprogramming to produce induced pluripotent stem cells (iPS cells) (Takahashi K, et al. (2007) Cell 131:861-872; Park I H, et al. (2008) Nature 451:141-146; Yu J, et al. (2007) Science 318:1917-1920; Kim D, et al. (2009) Cell Stem Cell 4:472-476; Soldner F, et al. (2009) Cell. 136:964-977; Huangfu D, et al. (2008) Nature Biotechnology 26:1269-1275; Li W, et al. (2009) Cell Stem Cell 4:16-19).

These methodologies, however, are characterized by a low reprogramming efficiency and in most cases, undesirable modification of the genome with integrating viral vectors. Higher efficiency methods, and methods that do not permanently modify the genome of the cell are of great interest.

Additional publications of interest include Stadtfeld et al. Science 322, 945-949 (2008); Okita et al. Science 322, 949-953 (2008); Kaji et al. Nature 458, 771-775 (2009); Soldner et al. Cell 136, 964-977 (2009); Woltjen et al. Nature 458, 766-770 (2009); Yu et al. Science (2009).

SUMMARY OF THE INVENTION

Compositions and methods are provided for producing induced human pluripotent stem cells (iPS cells). In some methods of the invention pluripotency is induced in somatic cells by introducing into the cells one or more minicircle DNA vector(s) encoding a plurality of reprogramming factors operably linked to a promoter; and maintaining the cells in culture for a period of time sufficient to reprogram the somatic cells to pluripotency. In certain embodiments a single minicircle DNA vector is utilized, where the vector comprises a plurality of reprogramming factor coding sequences, and where the combination of factors present on the single vector is sufficient to induce pluripotency.

Also provided are pluripotent stem cell populations comprising a minicircle vector, particularly a single minicircle DNA vector comprising a plurality of reprogramming factor coding sequences sufficient to induce pluripotency. The pluripotent stem cell populations may be provided as a cell culture, optionally a feeder-layer free cell culture. Various somatic cells find use in the methods; of particular interest are adipose-derived stem cells.

Minicircle vector compositions are provided, where the minicircle vector comprises one or a plurality of sequences encoding reprogramming factors. In some embodiments the vector comprises a plurality of reprogramming factor coding sequences, where the combination of factors present on the single vector is sufficient to induce pluripotency. The plurality of coding sequences may be operably linked to a single promoter, where coding sequences are separated by self-cleaving peptide sequences. A non-limiting example of factors sufficient to reprogram a somatic cell to pluripotency is: Oct4, Sox2, Lin28, and Nanog. An alternative non-limiting example of factors sufficient to reprogram a somatic cell to pluripotency is: Oct4, Sox2, c-Myc, and Klf4. In some embodiments, the minicircle vectors are optimized to remove expression-silencing bacterial sequences, where in many embodiments the vectors include a unidirectional site-specific recombination product sequence in addition to an expression cassette.

In other methods of the invention adipose-derived stem cells are induced to pluripotency by contacting a population of human somatic cells with a cocktail of reprogramming factors; and maintaining the cells in a feeder-layer free culture medium for a period of time sufficient to reprogram said human somatic cells to pluripotency.

The pluripotent cells derived by the methods of the invention may be used for transplantation, for experimental evaluation, as a source of lineage and cell specific products, and the like. These and other objects, advantages, and features of the invention will become apparent to those persons skilled in the art upon reading the details of the subject methods and compositions as more fully described below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is best understood from the following detailed description when read in conjunction with the accompanying drawings.

DETAILED DESCRIPTION OF THE INVENTION

Figure 1:
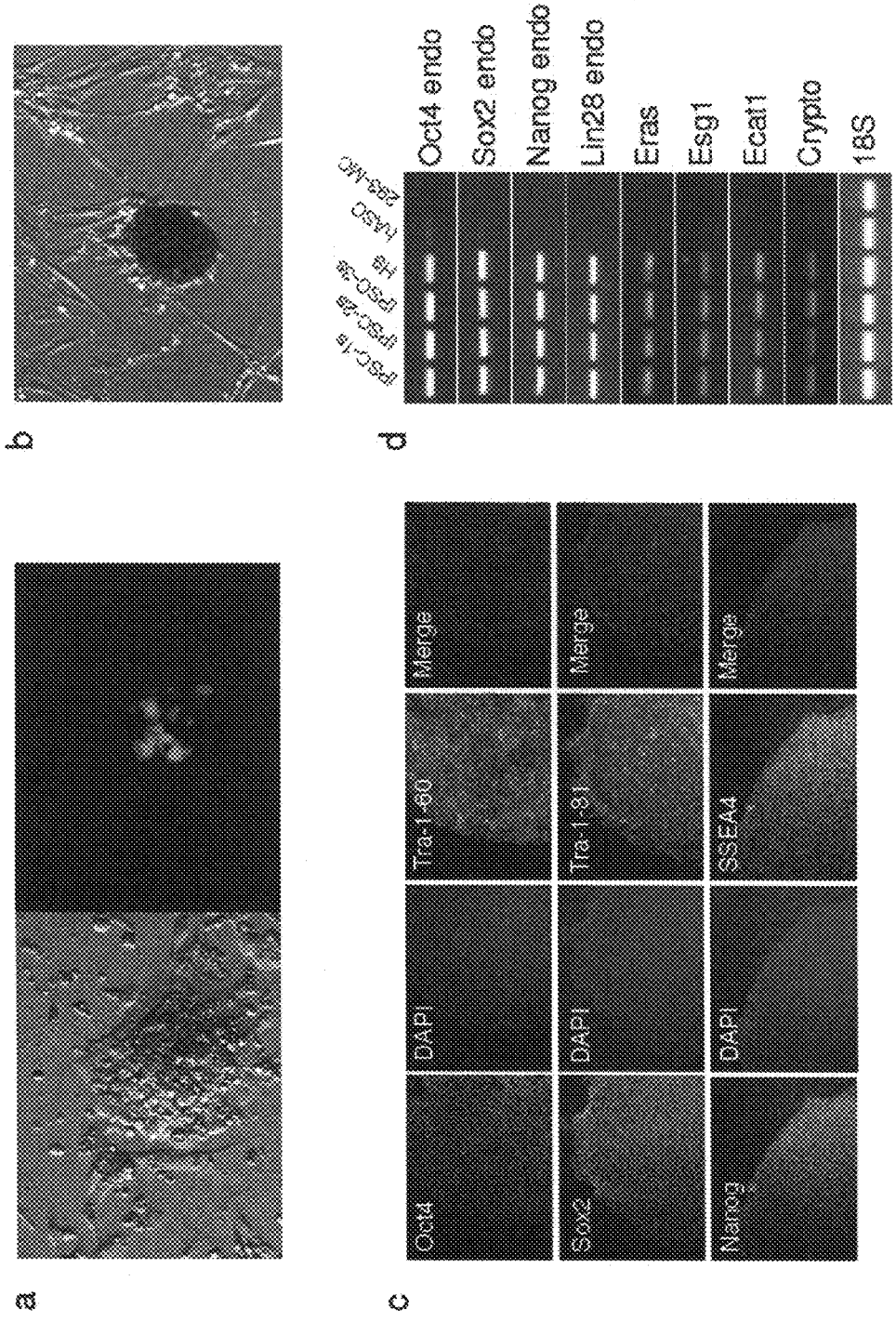
FIG. 1. Generation of iPS cells with minicircle vector. a, Representative day 18 cluster of mc-iPS cells. The cluster shown here exhibited transgene expression, as seen by GFP detection. GFP-negative colonies were isolated for further analysis. b, mc-iPS cells are positive for alkaline phosphatase, c, immunostain for common embryonic markers, and d, express embryonic genes, including reactivation of endogenous Oct4, Sox2, Nanog and Lin28. As negative control, 293FT cells were transfected with the minicircle vector (293-MC) but did not express the same endogenous genes. (Note: H9 is the H9 human ES cell line. iPSC-1s denotes a mc-iPS cell colony subclone derived from Donor 1, iPSC-2s subclone from Donor 2, etc). e, Bisulfate sequencing shows hypomethylation within the promoters of Oct4 and Nanog in the three mc-iPS cell subclones. f, Microarray data. Upper panel, heat map showing two mc-iPS cell subclones are similar to H7 human ES cells and distinct from hASCs. Lower panel, scatter plots highlighting Oct3/4, Sox2, and Nanog expression (red arrows). Green lines indicate 5-fold changes in expression levels between paired samples (iPSC represents the average of both subclones). g, Southern blot analysis of genomic DNA confirms that mc-iPS subclones are transgene free, as determined by the number of copies of Oct4 and Sox2. As positive control, lentivirally-reprogrammed iPS cells from the James Thomson lab (JT-iPSC) exhibited multiple bands for each of the two genes. h, mc-iPS cells had normal diploid karyotype.
Figure 1:
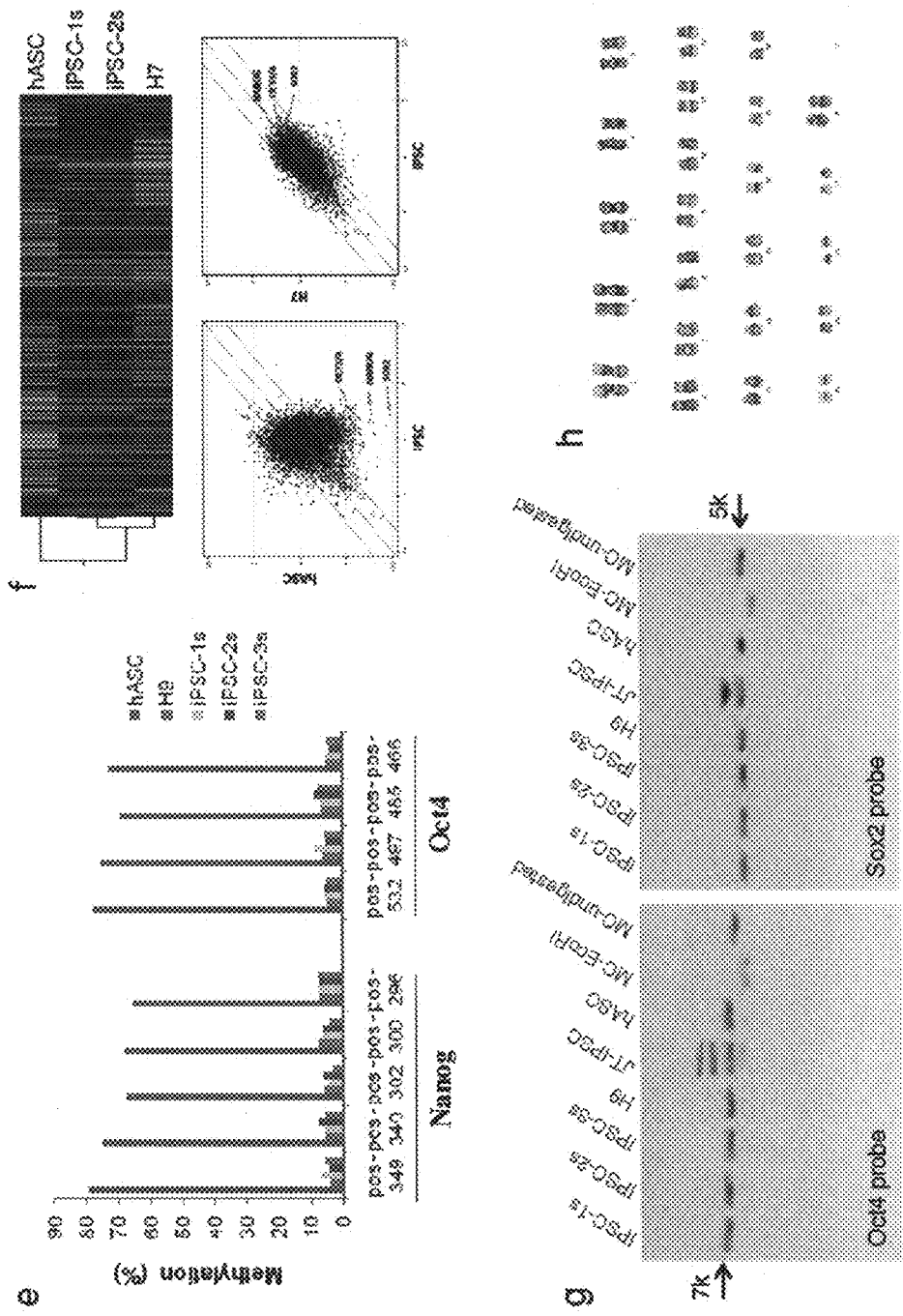

Before the present compositions and methods are described, it is to be understood that this invention is not limited to particular compositions and methods described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a reprogramming factor polypeptide" includes a plurality of such polypeptides, and reference to "the induced pluripotent stem cells" includes reference to one or more induced pluripotent stem cells and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

By "pluripotency" and pluripotent stem cells it is meant that such cells have the ability to differentiate into all types of cells in an organism. The term "induced pluripotent stem cell" encompasses pluripotent cells, that, like embryonic stem (ES) cells, can be cultured over a long period of time while maintaining the ability to differentiate into all types of cells in an organism, but that, unlike ES cells (which are derived from the inner cell mass of blastocysts), are derived from differentiated somatic cells, that is, cells that had a narrower, more defined potential and that in the absence of experimental manipulation could not give rise to all types of cells in the organism. By "having the potential to become iPS cells" it is meant that the differentiated somatic cells can be induced to become, i.e. can be reprogrammed to become, iPS cells. In other words, the somatic cell can be induced to redifferentiate so as to establish cells having the morphological characteristics, growth ability and pluripotency of pluripotent cells. iPS cells have an hESC-like morphology, growing as flat colonies with large nucleo-cytoplasmic ratios, defined borders and prominent nuclei. In addition, iPS cells express one or more key pluripotency markers known by one of ordinary skill in the art, including but not limited to Alkaline Phosphatase, SSEA3, SSEA4, Sox2, Oct3/4, Nanog, TRA160, TRA181, TDGF 1, Dnmt3b, FoxD3, GDF3, Cyp26a1, TERT, and zfp42. In addition, the iPS cells are capable of forming teratomas. In addition, they are capable of forming or contributing to ectoderm, mesoderm, or endoderm tissues in a living organism.

The terms "primary cells", "primary cell lines", and "primary cultures" are used interchangeably herein to refer to cells and cell cultures that have been derived from a subject and allowed to grow in vitro for a limited number of passages, i.e. splittings, of the culture. For example primary cultures are cultures that may have been passaged 0 times, 1 time, 2 times, 4 times, 5 times, 10 times, or 15 times, but not enough times go through the crisis stage. Typically, the primary adipose cells of the present invention are maintained for fewer than 10 passages in vitro prior to induction of pluripotency.

The term "efficiency of reprogramming" is used to refer to the ability of a primary cell culture to give rise to iPS cell colonies when contacted with reprogramming factors. Primary cell cultures that demonstrate an enhanced efficiency of reprogramming will demonstrate an enhanced ability to give rise to iPS cells when contacted with reprogramming factors relative to a control. The efficiency of reprogramming with the methods of the invention vary with the particular combination of somatic cells, method of introducing reprogramming factors, and method of culture following induction of reprogramming.

Where the somatic cells are adipose stem cells, an efficiency of reprogramming of about 0.1%, about 0.2% or greater may be obtained with conditions optimized for reprogramming efficiency, e.g. using viral vectors and feeder layers. However, conditions optimized for clinical use may provide for lower efficiency, including an efficiency of at least about 0.01%, about 0.02%, about 0.03% or greater where the cells are maintained in the absence of feeder layer cells following induction of reprogramming. The use of minicircle vectors may further reduce efficiency of reprogramming, including an efficiency of about 0.002%, about 0.002%, about 0.004%, about 0.005% or more.

A feature of utilizing adipose stem cells as a somatic cell for reprogramming is the shortened length of time required to observe cells having characteristics of pluripotent cells, where such cells may be observed 10, 11, 12, 13, 14, 15, 16 or more days following induction of reprogramming.

As used herein, "reprogramming factors", refers to one or more, i.e. a cocktail, of biologically active factors that act on a cell to alter transcription, thereby reprogramming a cell to multipotency or to pluripotency. Reprogramming factors may be provided to the cells of the subject invention individually or as a single composition, that is, as a premixed composition, of reprogramming factors. The factors may be provided at the same molar ratio or at different molar ratios. The factors may be provided once or multiple times in the course of culturing the cells of the subject invention. In some embodiments the reprogramming factor is a transcription factor, including without limitation, Oct3/4; Sox2; Klf4; c-Myc; Nanog; and Lin-28.

A Klf4 polypeptide is a polypeptide comprising the amino acid sequence that is at least 70% identical to the amino acid sequence of human Klf4, i.e., Kruppel-Like Factor 4 the sequence of which may be found at GenBank Accession Nos. NP_004226 and NM_004235. Klf4 polypeptides, e.g. those that are at least 70%, 75%, 80%, 85%, 90%, 91%, 92%, 95%, 97%, 99%, or 100% identical to the sequence provided in GenBank Accession No. NM_004235, and the nucleic acids that encode them find use as a reprogramming factor in the present invention.

A c-Myc polypeptide is a polypeptide comprising an amino acid sequence that is at least 70% identical to the amino acid sequence of human c-Myc, i.e., myelocytomatosis viral oncogene homolog, the sequence of which may be found at GenBank Accession Nos. NP_002458 and NM_002467. c-Myc polypeptides, e.g. those that are at least 70%, 75%, 80%, 85%, 90%, 91%, 92%, 95%, 97%, 99%, or 100% identical to the sequence provided in GenBank Accession No. NM_002467, and the nucleic acids that encode them find use as a reprogramming factor in the present invention.

A Nanog polypeptide is a polypeptide comprising an amino acid sequence that is at least 70% identical to the amino acid sequence of human Nanog, i.e., Nanog homeobox, the sequence of which may be found at GenBank Accession Nos. NP_079141 and NM_024865. Nanog polypeptides, e.g. those that are at least 70%, 75%, 80%, 85%, 90%, 91%, 92%, 95%, 97%, 99%, or 100% identical to the sequence provided in GenBank Accession No. NM_024865, and the nucleic acids that encode them find use as a reprogramming factor in the present invention.

A Lin-28 polypeptide is a polypeptide comprising an amino acid sequence that is at least 70% identical to the amino acid sequence of human Lin-28, i.e., Lin-28 homolog of *C. elegans*, the sequence of which may be found at GenBank Accession Nos. NP_078950 and NM_024674. Lin-28 polypeptides, e.g. those that are at least 70%, 75%, 80%, 85%, 90%, 91%, 92%, 95%, 97%, 99%, or 100% identical to the sequence provided in GenBank Accession No. NM_024674, and the nucleic acids that encode them find use as a reprogramming factor in the present invention.

An Oct3/4 polypeptide is a polypeptide comprising an amino acid sequence that is at least 70% identical to the amino acid sequence of human Oct 3/4, also known as *Homo sapiens* POU class 5 homeobox 1 (POU5F1) the sequence of which may be found at GenBank Accession Nos. NP_002692 and NM_002701. Oct3/4 polypeptides, e.g. those that are at least 70%, 75%, 80%, 85%, 90%, 91%, 92%, 95%, 97%, 99%, or 100% identical to the sequence provided in GenBank Accession No. NM_002701, and the nucleic acids that encode them find use as a reprogramming factor in the present invention.

A Sox2 polypeptide is a polypeptide comprising the amino acid sequence at least 70% identical to the amino acid sequence of human Sox2, i.e., sex-determining region Y-box 2 protein, the sequence of which may be found at GenBank Accession Nos. NP_003097 and NM_003106. Sox2 polypeptides, e.g. those that are at least 70%, 75%, 80%, 85%, 90%, 91%, 92%, 95%, 97%, 99%, or 100% identical to the sequence provided in GenBank Accession No. NM_003106, and the nucleic acids that encode them find use as a reprogramming factor in the present invention.

The terms "treatment", "treating", "treat" and the like are used herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a mammal, particularly a human, and includes: (a) preventing the disease or symptom from occurring in a subject which may be predisposed to the disease or symptom but has not yet been diagnosed as having it; (b) inhibiting the disease symptom, i.e., arresting its development; or (c) relieving the disease symptom, i.e., causing regression of the disease or symptom.

The terms "individual," "subject," "host," and "patient," are used interchangeably herein and refer to any mammalian subject for whom diagnosis, treatment, or therapy is desired, particularly humans.

Minicircle Vector. As used herein a minicircle vector is a small, double stranded circular DNA molecule that provides for persistent, high level expression of a sequence of interest that is present on the vector. For the purposes of the present invention the sequence of interest is a sequence encoding one or a plurality of reprogramming factors. The sequence of interest is operably linked to regulatory sequences present on the mini-circle vector, which regulatory sequences control its expression. Such mini-circle vectors are described, for example in published U.S. Patent Application US20040214329, herein specifically incorporated by reference.

The overall length of the subject minicircle vectors is sufficient to include the desired elements as described below, but not so long as to prevent or substantially inhibit to an unacceptable level the ability of the vector to enter the target cell upon contact with the cell, e.g., via systemic administration to the host comprising the cell. As such, the minicircle vector is generally at least about 0.3 kb long, often at least about 1.0 kb long, where the vector may be as long as 10 kb or longer, but in certain embodiments do not exceed this length.

The effective dose of a minicircle vector for introduction into cells may be empirically determined by one of skill in the art. For example, minicircle vectors may be provided to cells at a concentration of at least about 1 ng for $10^6$ cells, about 10 ng for $10^6$ cells, about 100 ng for $10^6$ cells, about 1 µg for $10^6$ cells, about 5 µg for $10^6$ cells, or more. Typically high concentrations are not deleterious.

Minicircle vectors differ from bacterial plasmid vectors in that they lack an origin of replication, and lack drug selection markers commonly found in bacterial plasmids, e.g. β-lactamase, tet, and the like. Consequently, minicircles are small in size, allowing more efficient delivery to a cell. More importantly, minicircles are devoid of the transgene expression silencing effect which is associated with the vector backbone nucleic acid sequences of parental plasmids from which the minicircle vectors are excised. The minicircle may be substantially free of vector sequences other than the recombinase hybrid product sequence, and the sequence of interest, i.e. a transcribed sequence and regulatory sequences required for expression.

A "vector" is capable of transferring nucleic acid sequences to target cells. For example, a vector may comprise a coding sequence capable of being expressed in a target cell. For the purposes of the present invention, "vector construct," "expression vector," and "gene transfer vector," generally refer to any nucleic acid construct capable of directing the expression of a gene of interest and which is useful in transferring the gene of interest into target cells. Thus, the term includes cloning and expression vehicles, as well as integrating vectors.

An "expression cassette" comprises any nucleic acid construct capable of directing the expression of any RNA transcript including gene/coding sequence of interest. Such cassettes can be constructed into a "vector," "vector construct," "expression vector," or "gene transfer vector," in order to transfer the expression cassette into target cells. Thus, the term includes cloning and expression vehicles, as well as viral vectors.

Expression vectors will contain a promoter that is recognized by the host organism and is operably linked to the reprogramming factor coding sequence. Promoters are untranslated sequences located upstream (5') to the start codon of a structural gene (generally within about 100 to 1000 bp) that control the transcription and translation of particular nucleic acid sequence to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. A large number of promoters recognized by a variety of potential host cells are well known. Both a native reprogramming factor polypeptide promoter sequence and many heterologous promoters may be used to direct expression of a reprogramming factor polypeptide. However, heterologous promoters are preferred, as they generally permit greater transcription and higher yields. Transcription by higher eukaryotes is often increased by inserting an enhancer sequence into the vector. Enhancers are cis-acting elements of DNA, usually about from 10 to 300 bp, which act on a promoter to increase its transcription. Enhancers are relatively orientation and position independent, having been found 5' and 3' to the transcription unit, within an intron, as well as within the coding sequence itself.

Expression vectors used in eukaryotic host cells may also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding Wnt polypeptide. Cells comprising the expression vector are grown under conditions that provide for expression of the desired polypeptide, which is then extracted from the cell lysate by conventional methods.

The minicircle vectors may comprise a product hybrid sequence of a unidirectional site-specific recombinase, which product hybrid sequence is the result of a unidirectional site specific recombinase mediated recombination of two recombinase substrate sequences as they are known in the art, e.g., attB and attP substrate sequences, and may be either the attR or attL product hybrid sequence. Typically, the product hybrid sequence ranges in length from about 10 to about 500 bp. In certain embodiments, the product sequence is a product hybrid sequence of a unidirectional site specific recombinase that is an integrase, where integrases of interest include, but are not limited to: wild-type phage integrases or mutants thereof, where specific representative integrases of interest include, but are not limited to: the integrases of ΦC31, R4, TP901-1, ΦBT1, Bxb1, RV-1, AA118, U153, ΦFC1, and the like.

Adipose-Derived Stem Cells. Adipose-derived stem cells or "adipose-derived stromal cells" refer to cells that originate from adipose tissue. By "adipose" is meant any fat tissue. The adipose tissue may be brown or white adipose tissue, derived from subcutaneous, omental/visceral, mammary, gonadal, or other adipose tissue site. Preferably, the adipose is subcutaneous white adipose tissue. Such cells may be provided as a primary cell culture or an immortalized cell line. The adipose tissue may be from any organism having fat tissue. Preferably, the adipose tissue is mammalian, most preferably the adipose tissue is human. A convenient source of adipose tissue is from liposuction surgery, however, the source of adipose tissue or the method of isolation of adipose tissue is not critical to the invention.

Adipose tissue offers many practical advantages for tissue engineering applications. It is abundant and accessible to harvest methods with minimal risk to the patient. It is estimated that there are more than $10^4$ stem cells per gram of adipose tissue (Sen et al 2001, Journal of Cellular Biochemistry 81:312-319), which cells can be used immediately or cryopreserved for future autologous or allogeneic applications.

Methods for the isolation, expansion, and differentiation of human adipose tissue-derived cells have been reported. See for example, Burris et al 1999, Mol Endocrinol 13:410-7; Erickson et al 2002, Biochem Biophys Res Commun. Jan. 18, 2002; 290(2):763-9; Gronthos et al 2001, Journal of Cellular Physiology, 189:54-63; Halvorsen et al 2001, Metabolism 50:407-413; Halvorsen et al 2001, Tissue Eng. 7(6):729-41; Harp et al 2001, Biochem Biophys Res Commun 281:907-912; Saladin et al 1999, Cell Growth & Diff 10:43-48; Sen et al 2001, Journal of Cellular Biochemistry 81:312-319; Zhou et al 1999, Biotechnol. Techniques 13: 513-517. Adipose tissue-derived stromal cells may be obtained from minced human adipose tissue by collagenase digestion and differential centrifugation [Halvorsen et al 2001, Metabolism 50:407-413; Hauner et al 1989, J Clin Invest 84:1663-1670; Rodbell et al 1966, J Biol Chem 241:130-139].

Adipose tissue derived stem cells have been reported to express markers including: CD13, CD29, CD44, CD63, CD73, CD90, CD166, aldehyde dehydrogenase (ALDH), and ABCG2. The adipose tissue derived stem cells may be a population of purified mononuclear cells extracted from adipose tissue capable of proliferating in culture for more than 1 month.

For isolation of cells from tissue, an appropriate solution may be used for dispersion or suspension. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc.

The cell population may be used immediately. Alternatively, the cell population may be frozen at liquid nitrogen temperatures and stored for long periods of time, being thawed and capable of being reused. In such cases, the cells will usually be frozen in 10% DMSO, 50% serum, 40% buffered medium, or some other such solution as is commonly used in the art to preserve cells at such freezing temperatures, and thawed in a manner as commonly known in the art for thawing frozen cultured cells.

The adipose cells may be cultured in vitro under various culture conditions. Culture medium may be liquid or semi-solid, e.g. containing agar, methylcellulose, etc. The cell population may be conveniently suspended in an appropriate nutrient medium, such as Iscove's modified DMEM or RPMI-1640, normally supplemented with fetal calf serum (about 5-10%), L-glutamine, a thiol, particularly 2-mercaptoethanol, and antibiotics, e.g. penicillin and streptomycin. In one embodiment of the invention, the adipose cells are maintained in culture in the absence of feeder layer cells, i.e. in the absence of.

The culture may contain growth factors to which the cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors.

Methods of Inducing Pluripotency

Somatic cells, particularly somatic cells that are adipose stem cells, are contacted with reprogramming factors, as defined above, in a combination and quantity sufficient to reprogram the cell to pluripotency. Reprogramming factors may be provided to the somatic cells individually or as a single composition, that is, as a premixed composition, of reprogramming factors. In preferred embodiments the reprogramming factors are provided as a plurality of coding sequences on a single minicircle vector; although in some embodiments other methods of providing the factors are utilized, particularly where the somatic cells are adipose stem cells.

The reprogramming factors may be added to the subject cells simultaneously or sequentially at different times. In some embodiments, a set of at least three purified reprogramming factor is added, e.g., an Oct3/4 polypeptide, a Sox2 polypeptide, and a Klf4, c-myc, nanog or lin28 polypeptide. In some embodiments, a set of four purified reprogramming factors is provided to the cells e.g., an Oct3/4 polypeptide, a Sox2 polypeptide, a Klf4 polypeptide and a c-Myc polypeptide; or an Oct3/4 polypeptide, a Sox2 polypeptide, a lin28 polypeptide and a nanog polypeptide.

Where the reprogramming factors are provided in the form of a minicircle vector the somatic cells are contacted with the vectors such that the vectors are taken up by the cells. Methods for contacting cells with nucleic acid vectors, such as nucleofection, electroporation, calcium chloride transfection, and lipofection, are well known in the art.

Alternative methods for introducing the reprogramming factors to adipose stem cells include providing a cell with purified protein factors. Typically, a reprogramming factor polypeptide will comprise the polypeptide sequences of the reprogramming factor fused to a polypeptide permeant domain. A number of permeant domains are known in the art and may be used in the nuclear acting, non-integrating polypeptides of the present invention, including peptides, peptidomimetics, and non-peptide carriers. For example, a permeant peptide may be derived from the third alpha helix of *Drosophila melanogaster* transcription factor Antennapaedia, referred to as penetratin, which comprises the amino acid sequence RQIKIWFQNRRMKWKK (SEQ ID NO:53). As another example, the permeant peptide comprises the HIV-1 tat basic region amino acid sequence, which may include, for example, amino acids 49-57 of naturally-occurring tat protein. Other permeant domains include poly-arginine motifs, for example, the region of amino acids 34-56 of HIV-1 rev protein, nona-arginine, octa-arginine, and the like. (See, for example, Futaki et al. (2003) Curr Protein Pept Sci. 2003 April; 4(2): 87-96; and Wender et al. (2000) Proc. Natl. Acad. Sci. U.S.A 2000 Nov. 21; 97(24):13003-8; published U.S. Patent applications 20030220334; 20030083256; 20030032593; and 20030022831, herein specifically incorporated by reference for the teachings of translocation peptides and peptoids). The nona-arginine (R9) sequence is one of the more efficient PTDs that have been characterized (Wender et al. 2000; Uemura et al. 2002). In such embodiments, cells are incubated in the presence of a purified reprogramming factor polypeptide for about 30 minutes to about 24 hours, e.g., 1 hours, 1.5 hours, 2 hours, 2.5 hours, 3 hours, 3.5 hours 4 hours, 5 hours, 6 hours, 7 hours, 8 hours, 12 hours, 16 hours, 18 hours, 20 hours, or any other period from about 30 minutes to about 24 hours. Typically, the reprogramming factors are provided to the subject cells once, and the cells are allowed to incubate with the reprogramming factors for 16-24 hours, after which time the media is replaced with fresh media and the cells are cultured further, or the reprogramming factors are provided to the subject cells twice, with two 16-24 hour incubations with the recombination factors following each provision, after which the media is replaced with fresh media and the cells are cultured further.

In some embodiments, reprogramming factors are provided to adipose stem cells as nucleic acids other than minicircle vectors. Many vectors useful for transferring exogenous genes into target mammalian cells are available. The vectors may be maintained episomally, e.g. as plasmids, virus-derived vectors such cytomegalovirus, adenovirus, etc., or they may be integrated into the target cell genome, through homologous recombination or random integration, e.g. retrovirus derived vectors such as MMLV, HIV-1, ALV, etc.

Alternatively, nucleic acids encoding the reprogramming factors may be provided to the subject via a virus, where the somatic cells are contacted with viral particles comprising nucleic acids encoding the reprogramming factors. Retroviruses, for example, lentiviruses, are particularly suitable to the method of the invention, as they can be used to transfect non-dividing cells (see, for example, Uchida et al. (1998) P.N.A.S. 95(20):11939-44). Commonly used retroviral vectors are "defective", i.e. unable to produce viral proteins required for productive infection. Rather, replication of the vector requires growth in a packaging cell line.

Vectors used for providing reprogramming factors to the subject cells as nucleic acids will typically comprise suitable promoters for driving the expression, that is, transcriptional activation, of the reprogramming factor nucleic acids. This may include ubiquitously acting promoters, for example, the CMV-β-actin promoter, or inducible promoters, such as promoters that are active in particular cell populations or that respond to the presence of drugs such as tetracycline. By transcriptional activation, it is intended that transcription will be increased above basal levels in the target cell by at least about 10 fold, by at least about 100 fold, more usually by at least about 1000 fold. In addition, vectors used for providing reprogramming factors to the subject cells may include genes that must later be removed, e.g. using a recombinase system such as Cre/Lox, or the cells that express them destroyed, e.g. by including genes that allow selective toxicity such as herpesvirus TK, bcl-xs, etc.

Following introduction of reprogramming factors, the somatic cells may be maintained in a conventional culture medium comprising feeder layer cells, or may be cultured in the absence of feeder layers, i.e. lacking somatic cells other than those being induced to pluripotency. Feeder layer free cultures may utilize a protein coated surface, e.g. matrigel, etc.

iPS cells induced to become such by the methods of the invention have an hESC-like morphology, growing as flat colonies with large nucleo-cytoplasmic ratios, defined borders and prominent nuclei. In addition, the iPS cells may express one or more key pluripotency markers known by one of ordinary skill in the art, including but not limited to Alkaline Phosphatase, SSEA3, SSEA4, Sox2, Oct3/4, Nanog, TRA160, TRA181, TDGF 1, Dnmt3b, FoxD3, GDF3, Cyp26a1, TERT, and zfp42. In addition, the iPS cells are capable of forming teratomas. In addition, they are capable of forming or contributing to ectoderm, mesoderm, or endoderm tissues in a living organism.

Genes may be introduced into the somatic cells or the iPS cells derived therefrom for a variety of purposes, e.g. to replace genes having a loss of function mutation, provide marker genes, etc. Alternatively, vectors are introduced that express antisense mRNA or ribozymes, thereby blocking expression of an undesired gene. Other methods of gene therapy are the introduction of drug resistance genes to enable normal progenitor cells to have an advantage and be subject to selective pressure, for example the multiple drug resistance gene (MDR), or anti-apoptosis genes, such as bcl-2. Various techniques known in the art may be used to introduce nucleic acids into the target cells, e.g. electroporation, calcium precipitated DNA, fusion, transfection, lipofection, infection and the like, as discussed above. The particular manner in which the DNA is introduced is not critical to the practice of the invention.

To prove that one has genetically modified the somatic cells or the iPS cells derived therefrom, various techniques may be employed. The genome of the cells may be restricted and used with or without amplification. The polymerase chain reaction; gel electrophoresis; restriction analysis; Southern, Northern, and Western blots; sequencing; or the like, may all be employed. The cells may be grown under various conditions to ensure that the cells are capable of maturation to all of the myeloid lineages while maintaining the ability to express the introduced DNA. Various tests in vitro and in vivo may be employed to ensure that the pluripotent capability of the cells has been maintained.

The iPS cells produced by the above methods may be used for reconstituting or supplementing differentiating or differentiated cells in a recipient. The induced cells may be differentiated into cell-types of various lineages. Examples of differentiated cells include any differentiated cells from ectodermal (e.g., neurons and fibroblasts), mesodermal (e.g., cardiomyocytes), or endodermal (e.g., pancreatic cells) lineages. The differentiated cells may be one or more: pancreatic beta cells, neural stem cells, neurons (e.g., dopaminergic neurons), oligodendrocytes, oligodendrocyte progenitor cells, hepatocytes, hepatic stem cells, astrocytes, myocytes, hematopoietic cells, or cardiomyocytes.

The differentiated cells derived from the induced cells may be terminally differentiated cells, or they may be capable of giving rise to cells of a specific lineage. For example, induced cells can be differentiated into a variety of multipotent cell types, e.g., neural stem cells, cardiac stem cells, or hepatic stem cells. The stem cells may then be further differentiated into new cell types, e.g., neural stem cells may be differentiated into neurons; cardiac stem cells may be differentiated into cardiomyocytes; and hepatic stem cells may be differentiated into hepatocytes.

There are numerous methods of differentiating the induced cells into a more specialized cell type. Methods of differentiating induced cells may be similar to those used to differentiate stem cells, particularly ES cells, MSCs, MAPCs, MIAMI, hematopoietic stem cells (HSCs). In some cases, the differentiation occurs ex vivo; in some cases the differentiation occurs in vivo.

Any known method of generating neural stem cells from ES cells may be used to generate neural stem cells from induced cells, See, e.g., Reubinoff et al., (2001), Nat, Biotechnol., 19(12): 1134-40. For example, neural stem cells may be generated by culturing the induced cells as floating aggregates in the presence of noggin, or other bone morphogenetic protein antagonist, see e.g., Itsykson et al., (2005), Mol, Cell Neurosci., 30(1):24-36. In another example, neural stem cells may be generated by culturing the induced cells in suspension to form aggregates in the presence of growth factors, e.g., FGF-2, Zhang et al., (2001), Nat. Biotech., (19): 1129-1133. In some cases, the aggregates are cultured in serum-free medium containing FGF-2. In another example, the induced cells are co-cultured with a mouse stromal cell line, e.g., PA6 in the presence of serum-free medium comprising FGF-2. In yet another example, the induced cells are directly transferred to serum-free medium containing FGF-2 to directly induce differentiation.

Neural stems derived from the induced cells may be differentiated into neurons, oligodendrocytes, or astrocytes. Often, the conditions used to generate neural stem cells can also be used to generate neurons, oligodendrocytes, or astrocytes.

Dopaminergic neurons play a central role in Parkinson's Disease and other neurodegenerative diseases and are thus of particular interest. In order to promote differentiation into dopaminergic neurons, induced cells may be co-cultured with a PA6 mouse stromal cell line under serum-free conditions, see, e.g., Kawasaki et al., (2000) Neuron, 28(1):3140. Other methods have also been described, see, e.g., Pomp et al., (2005), Stem Cells 23(7):923-30; U.S. Pat. No. 6,395,546, e.g., Lee et al., (2000), Nature Biotechnol., 18:675-679.

Oligodendrocytes may also be generated from the induced cells. Differentiation of the induced cells into oligodendrocytes may be accomplished by known methods for differentiating ES cells or neural stem cells into oligodendrocytes. For example, oligodendrocytes may be generated by co-culturing induced cells or neural stem cells with stromal cells, e.g., Hermann et al. (2004), J Cell Sci. 117(Pt 19):4411-22. In another example, oligodendrocytes may be generated by culturing the induced cells or neural stem cells in the presence of a fusion protein, in which the Interleukin (IL)-6 receptor, or derivative, is linked to the IL-6 cytokine, or derivative thereof. Oligodendrocytes can also be generated from the induced cells by other methods known in the art, see, e.g. Kang et al., (2007) Stem Cells 25, 419-424.

Astrocytes may also be produced from the induced cells. Astrocytes may be generated by culturing induced cells or neural stem cells in the presence of neurogenic medium with bFGF and EGF, see e.g., Brustle et al., (1999), Science, 285:754-756.

Induced cells may be differentiated into pancreatic beta cells by methods known in the art, e.g., Lumelsky et al., (2001) Science, 292:1389-1394; Assady et al., (2001), Diabetes, 50:1691-1697; D'Amour et al., (2006), Nat. Biotechnol., 24:1392-1401; D'Amour et al., (2005), Nat. Biotechnol. 23:1534-1541. The method may comprise culturing the induced cells in serum-free medium supplemented with Activin A, followed by culturing in the presence of serum-free medium supplemented with all-trans retinoic acid, followed by culturing in the presence of serum-free medium supplemented with bFGF and nicotinamide, e.g., Jiang et al., (2007), Cell Res., 4:333-444. In other examples, the method comprises culturing the induced cells in the presence of serum-free medium, activin A, and Wnt protein from about 0.5 to about 6 days, e.g., about 0.5, 1, 2, 3, 4, 5, 6, days; followed by culturing in the presence of from about 0.1% to about 2%, e.g., 0.2%, FBS and activin A from about 1 to about 4 days, e.g., about 1, 2, 3, or 4 days; followed by culturing in the presence of 2% FBS, FGF-10, and KAAD-cyclopamine (keto-N-aminoethylaminocaproyl dihydro cinnamoylcyclopamine) and retinoic acid from about 1 to about 5 days, e.g., 1, 2, 3, 4, or 5 days; followed by culturing with 1% B27, gamma secretase inhibitor and extendin-4 from about 1 to about 4 days, e.g., 1, 2, 3, or 4 days; and finally culturing in the presence of 1% B27, extendin-4, IGF-1, and HGF for from about 1 to about 4 days, e.g., 1, 2, 3, or 4 days.

Hepatic cells or hepatic stem cells may be differentiated from the induced cells. For example, culturing the induced cells in the presence of sodium butyrate may generate hepatocytes, see e.g., Rambhatla et al., (2003), Cell Transplant, 12:1-11. In another example, hepatocytes may be produced by culturing the induced cells in serum-free medium in the presence of Activin A, followed by culturing the cells in fibroblast growth factor-4 and bone morphogenetic protein-2, e.g., Cai et al., (2007), Hepatology, 45(5): 1229-39. In an exemplary embodiment, the induced cells are differentiated into hepatic cells or hepatic stem cells by culturing the induced cells in the presence of Activin A from about 2 to about 6 days, e.g., about 2, about 3, about 4, about 5, or about 6 days, and then culturing the induced cells in the presence of hepatocyte growth factor (HGF) for from about 5 days to about 10 days, e.g., about 5, about 6, about 7, about 8, about 9, or about 10 days.

The induced cells may also be differentiated into cardiac muscle cells. Inhibition of bone morphogenetic protein (BMP) signaling may result in the generation of cardiac muscle cells (or cardiomyocytes), see, e.g., Yuasa et al., (2005), Nat. Biotechnol., 23(5):607-11. Thus, in an exemplary embodiment, the induced cells are cultured in the presence of noggin for from about two to about six days, e.g., about 2, about 3, about 4, about 5, or about 6 days, prior to allowing formation of an embryoid body, and culturing the embryoid body for from about 1 week to about 4 weeks, e.g., about 1, about 2, about 3, or about 4 weeks.

In other examples, cardiomyocytes may be generated by culturing the induced cells in the presence of leukemia inhibitory factor (LIF), or by subjecting them to other methods known in the art to generate cardiomyocytes from ES cells, e.g., Bader et al., (2000), Circ. Res., 86:787-794, Kehat et al., (2001), J. Clin. Invest., 108:407-414; Mummery et al., (2003), Circulation, 107:2733-2740.

Examples of methods to generate other cell-types from induced cells include: (1) culturing induced cells in the presence of retinoic acid, leukemia inhibitory factor (LIF), thyroid hormone (T3), and insulin in order to generate adipocytes, e.g., Dani et al., (1997), J. Cell Sci., 110:1279-1285; (2) culturing induced cells in the presence of BMP-2 or BMP4 to generate chondrocytes, e.g., Kramer et al., (2000), Mech. Dev., 92:193-205; (3) culturing the induced cells under conditions to generate smooth muscle, e.g., Yamashita et al., (2000), Nature, 408:92-96; (4) culturing the induced cells in the presence of beta-1 integrin to generate keratinocytes, e.g., Bagutti et al., (1996), Dev. Biol., 179:184-196; (5) culturing the induced cells in the presence of Interleukin-3 (IL-3) and macrophage colony stimulating factor to generate macrophages, e.g., Lieschke and Dunn (1995), Exp. Hemat., 23:328-334; (6) culturing the induced cells in the presence of IL-3 and stem cell factor to generate mast cells, e.g., Tsai et al., (2000), Proc. Natl. Acad. Sci. USA, 97:9186-9190; (7) culturing the induced cells in the presence of dexamethasone and stromal cell layer, steel factor to generate melanocytes, e.g., Yamane et al., (1999), Dev. Dyn., 216:450-458; (8) co-culturing the induced cells with fetal mouse osteoblasts in the presence of dexamethasone, retinoic acid, ascorbic acid, beta-glycerophosphate to generate osteoblasts, e.g., Buttery et al., (2001), Tissue Eng., 7:89-99; (9) culturing the induced cells in the presence of osteogenic factors to generate osteoblasts, e.g., Sottile et al., (2003), Cloning Stem Cells, 5:149-155; (10) overexpressing insulin-like growth factor-2 in the induced cells and culturing the cells in the presence of dimethyl sulfoxide to generate skeletal muscle cells, e.g., Prelle et al., (2000), Biochem. Biophys. Res. Commun., 277:631-638; (11) subjecting the induced cells to conditions for generating white blood cells; or (12) culturing the induced cells in the presence of BMP4 and one or more: SCF, FLT3, IL-3, IL-6, and GCSF to generate hematopoietic progenitor cells, e.g., Chadwick et al., (2003), Blood, 102:906-915.

In some cases, sub-populations of differentiated cells may be purified or isolated. In some cases, one or more monoclonal antibodies specific to the desired cell type are incubated with the cell population and those bound cells are isolated. In other cases, the desired subpopulation of cells expresses a reporter gene that is under the control of a cell type specific promoter.

In a specific embodiment, the hygromycin B phosphotransferase-EGFP fusion protein is expressed in a cell type specific manner. The method of purifying comprises sorting the cells to select green fluorescent cells and reiterating the sorting as necessary, in order to obtain a population of cells enriched for cells expressing the construct (e.g., hygromycin B phosphotransferase-EGFP) in a cell-type-dependent manner. Selection of desired sub-populations of cells may also be accomplished by negative selection of proliferating cells with the herpes simplex virus thymidine kinase/ganciclovir (HS-Vtk/GCV) suicide gene system or by positive selection of cells expressing a bicistronic reporter, e.g., Anderson et al. (2007) Mol. Ther. (11):2027-2036.

The induced cells, or cells differentiated from the induced cells, may be used as a therapy to treat disease (e.g., a genetic defect). The therapy may be directed at treating the cause of the disease; or alternatively, the therapy may be to treat the effects of the disease or condition. The induced cells may be transferred to, or close to, an injured site in a subject; or the cells can be introduced to the subject in a manner allowing the cells to migrate, or home, to the injured site. The transferred cells may advantageously replace the damaged or injured cells and allow improvement in the overall condition of the subject. In some instances, the transferred cells may stimulate tissue regeneration or repair.

The transferred cells may be cells differentiated from induced cells. The transferred cells also may be multipotent stem cells differentiated from the induced cells. In some cases, the transferred cells may be induced cells that have not been differentiated.

The number of administrations of treatment to a subject may vary. Introducing the induced and/or differentiated cells into the subject may be a one-time event; but in certain situations, such treatment may elicit improvement for a limited period of time and require an on-going series of repeated treatments. In other situations; multiple administrations of the cells may be required before an effect is observed. The exact protocols depend upon the disease or condition, the stage of the disease and parameters of the individual subject being treated.

The cells may be introduced to the subject via any of the following routes: parenteral, intravenous, intraarterial, intramuscular, subcutaneous, transdermal, intratracheal, intraperitoneal, or into spinal fluid.

The induced cells may be differentiated into cells and then transferred to subjects suffering from a wide range of diseases or disorders. Subjects suffering from neurological diseases or disorders could especially benefit from stem cell therapies. In some approaches, the induced cells may be differentiated into neural stem cells or neural cells and then transplanted to an injured site to treat a neurological condition, e.g., Alzheimer's disease, Parkinson's disease, multiple sclerosis, cerebral infarction, spinal cord injury, or other central nervous system disorder, see, e.g., Morizane et al., (2008), Cell Tissue Res., 331(1):323-326; Coutts and Keirstead (2008), Exp. Neurol., 209(2):368-377; Goswami and Rao (2007), Drugs, 10(10):713-719.

For the treatment of Parkinson's disease, the induced cells may be differentiated into dopamine-acting neurons and then transplanted into the striate body of a subject with Parkinson's disease. For the treatment of multiple sclerosis, neural stem cells may be differentiated into oligodendrocytes or progenitors of oligodendrocytes, which are then transferred to a subject suffering from MS.

For the treatment of any neurologic disease or disorder, a successful approach may be to introduce neural stem cells to the subject. For example, in order to treat Alzheimer's disease, cerebral infarction or a spinal injury, the induced cells may be differentiated into neural stem cells followed by transplantation into the injured site. The induced cells may also be engineered to respond to cues that can target their migration into lesions for brain and spinal cord repair, e.g., Chen et al., (2007), Stem Cell Rev., 3(4):280-288.

Diseases other then neurological disorders may also be treated by a stem cell therapy that uses cells differentiated from induced cells, e.g., induced multipotent or pluripotent stem cells. Degenerative heart diseases such as ischemic cardiomyopathy, conduction disease, and congenital defects could benefit from stem cell therapies, see, e.g. Janssens et al., (2006), Lancet, 367:113-121.

Pancreatic islet cells (or primary cells of the islets of Langerhans) may be transplanted into a subject suffering from diabetes (e.g., diabetes mellitus, type 1), see e.g., Burns et al., (2006) Curr. Stem Cell Res. Ther., 2:255-266. In some embodiments, pancreatic beta cells derived from induced cells may be transplanted into a subject suffering from diabetes (e.g., diabetes mellitus, type 1).

In other examples, hepatic cells or hepatic stem cells derived from induced cells are transplanted into a subject suffering from a liver disease, e.g., hepatitis, cirrhosis, or liver failure.

Hematopoietic cells or hematopoietic stem cells (HSCs) derived from induced cells may be transplanted into a subject suffering from cancer of the blood, or other blood or immune disorder. Examples of cancers of the blood that are potentially treated by hematopoietic cells or HSCs include: acute lymphoblastic leukemia, acute myeloblastic leukemia, chronic myelogenous leukemia (CML), Hodgkin's disease, multiple myeloma, and non-Hodgkin's lymphoma. Often, a subject suffering from such disease must undergo radiation and/or chemotherapeutic treatment in order to kill rapidly dividing blood cells. Introducing HSCs derived from induced cells to these subjects may help to repopulate depleted reservoirs of cells.

In some cases, hematopoietic cells or HSCs derived from induced cells may also be used to directly fight cancer. For example, transplantation of allogeneic HSCs has shown promise in the treatment of kidney cancer, see, e.g., Childs et al., (2000), N. Engl. J. Med., 343:750-758. In some embodiments, allogeneic, or even autologous, HSCs derived from induced cells may be introduced into a subject in order to treat kidney or other cancers.

Hematopoietic cells or HSCs derived from induced cells may also be introduced into a subject in order to generate or repair cells or tissue other than blood cells, e.g., muscle, blood vessels, or bone. Such treatments may be useful for a multitude of disorders.

In some cases, the induced cells are transferred into an immunocompromised animal, e.g., SCID mouse, and allowed to differentiate. The transplanted cells may form a mixture of differentiated cell types and tumor cells. The specific differentiated cell types of interest can be selected and purified away from the tumor cells by use of lineage specific markers, e.g., by fluorescent activated cell sorting (FACS) or other sorting method, e.g., magnetic activated cell sorting (MACS). The differentiated cells may then be transplanted into a subject (e.g., an autologous subject, HLA-matched subject) to treat a disease or condition. The disease or condition may be a hematopoietic disorder, an endocrine deficiency, degenerative neurologic disorder, hair loss, or other disease or condition described herein.

The iPS cells may be administered in any physiologically acceptable medium. They may be provided alone or with a suitable substrate or matrix, e.g. to support their growth and/or organization in the tissue to which they are being transplanted. Usually, at least $1\times10^5$ cells will be administered, preferably $1\times10^6$ or more. The cells may be introduced by injection, catheter, or the like. The cells may be frozen at liquid nitrogen temperatures and stored for long periods of time, being capable of use on thawing. If frozen, the cells will usually be stored in a 10% DMSO, 50% FCS, 40% RPMI 1640 medium. Once thawed, the cells may be expanded by use of growth factors and/or stromal cells associated with progenitor cell proliferation and differentiation.

Kits may be provided, where the kit will comprise staining reagents that are sufficient to differentially identify the subject SSEA3+ differentiated somatic cells described herein. A combination of interest may include one or more reagents specific for the marker or combination of markers of the present invention, and may further include staining reagents specific for other proteins that mark the subject cells, e.g. Nanog. The staining reagents are preferably antibodies, and may be detectably labeled. Kits may also include tubes, buffers, etc., and instructions for use.

Each publication cited in this specification is hereby incorporated by reference in its entirety for all purposes.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention, which will be limited only by the appended claims.

As used herein the singular forms "a", "and", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Minicircle DNA Induces Pluripotency in Adult Human Cells

Due to the risk of insertional mutagenesis, viral transduction has been increasingly replaced by non-viral methods to generate induced pluripotent stem (iPS) cells. One technique that has not yet been explored is the use of "minicircle" DNA, a novel compact vector that is free of bacterial DNA and capable of persistent high level expression in cells. Here, we report the use of a single minicircle vector to generate transgene-free iPS cells from adult human cells.

Non-viral methods for generating iPS cells using adenovirus, plasmids, or excision of reprogramming factors using Cre/LoxP or piggyBAC transposition have been reported, but in general are restricted to mouse, suffer from low reprogramming efficiencies (<0.003%), and may leave behind residual vector sequences. Recently, successful reprogramming of human cells was reported using episomal vectors derived from the Epstein-Barr virus. However, this technique required three individual plasmids carrying a total of seven factors, including the oncogene SV40, and resulted in very low yields (<0.0006%). Further, expression of the EBNA1 protein, as was required for this technique, may increase immune cell recognition of transfected cells, thus potentially limiting clinical application if the transgene is not completely removed. Protein-based iPS cell generation in mouse and human cells has also been published, but required either chemical treatment (valproic acid) or greater than four rounds of treatment. Further, protein-based methods necessitate expertise in protein chemistry and handling—skills that many laboratories do not have. Most DNA-based methods require only minimal molecular biology background, and so remain a more attractive option for a wider population of researchers interested in cellular reprogramming.

Figure 3:
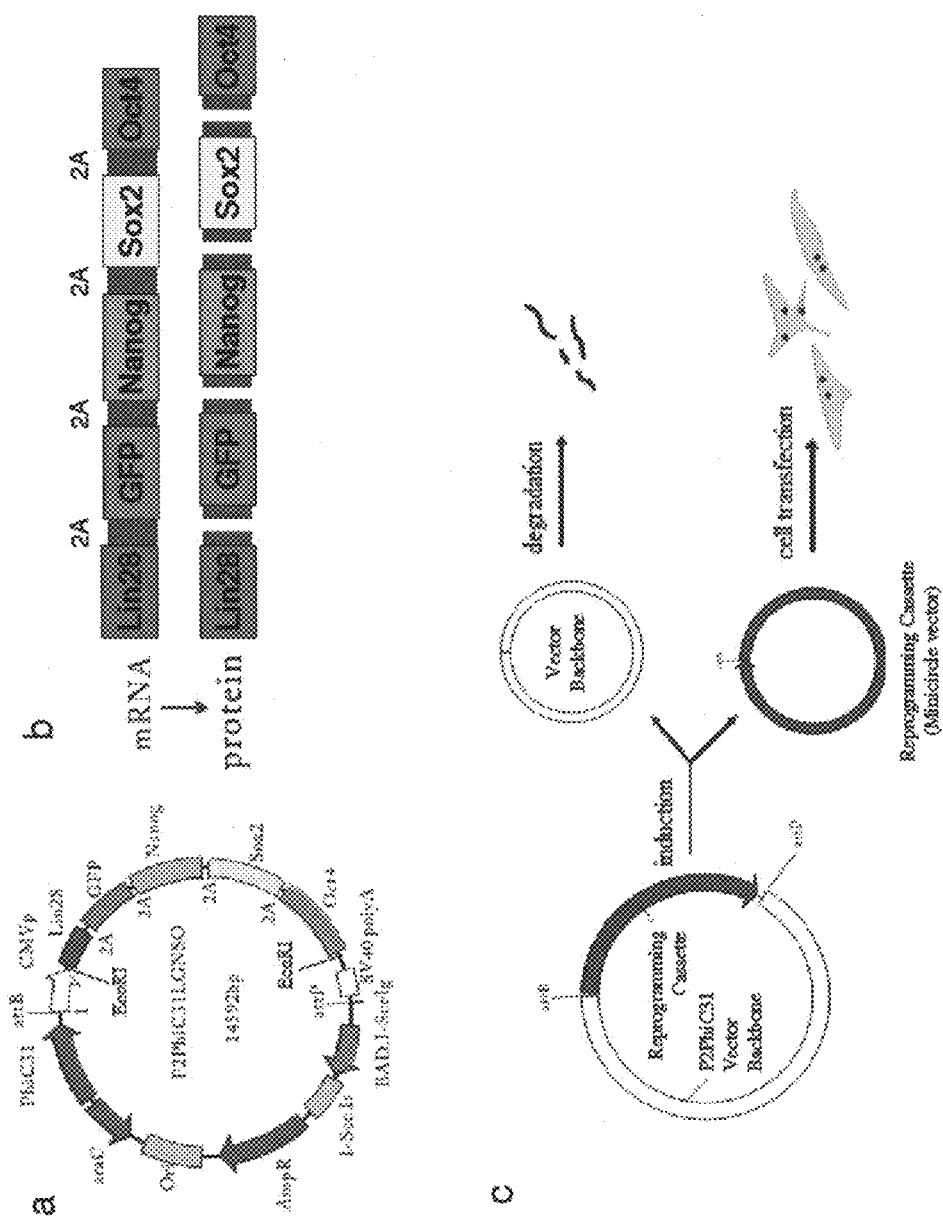
FIG. 3. Map of the P2PhiC31-LGNSO plasmid and schematic of minicircle DNA generation. a, The reprogramming cassette is driven by a CMV promoter and mounted in a minicircle DNA vector (P2PhiC31). Lin28, GFP, Nanog, Sox2, and Oct4 coding regions are linked by 2A peptide sequences. b, The four reprogramming factors and GFP are transcribed into a single messenger RNA, then translated into individual proteins mediated by self-cleavage peptide 2A. c, The minicircle vector, when delivered into *E. coli* and cultured under induction conditions, can be purified by removing the bacteria elements and leaving just the reprogramming cassette.
Figure 4:
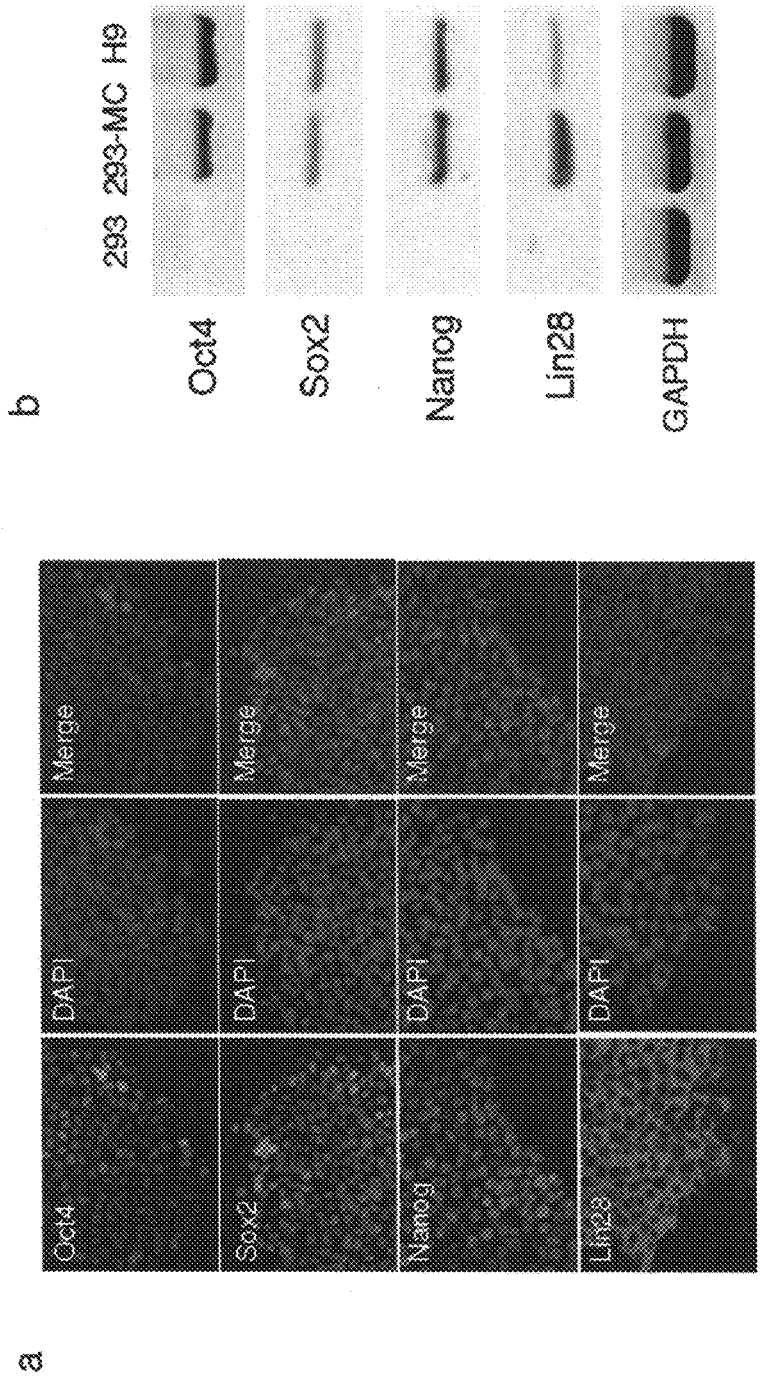
FIG. 4. Validation of reprogramming factor co-expression after minicircle DNA transfection of 293FT cells. a, Immunofluorescence demonstrates co-expression of Oct4, Sox2, Nanog, and Lin28. Note that Oct4, Sox2, and Nanog are primarily nuclear-localized, whereas Lin28 is in the cytoplasm, as expected. b, Western blot confirms the expression of individual proteins in minicircle-transfected 293FT cells (293-MC). Transfected cells expressed the proteins at levels similar to H9 human ES cells (H9). 293FT cells without minicircle (293) were used as negative control.
Figure 5:
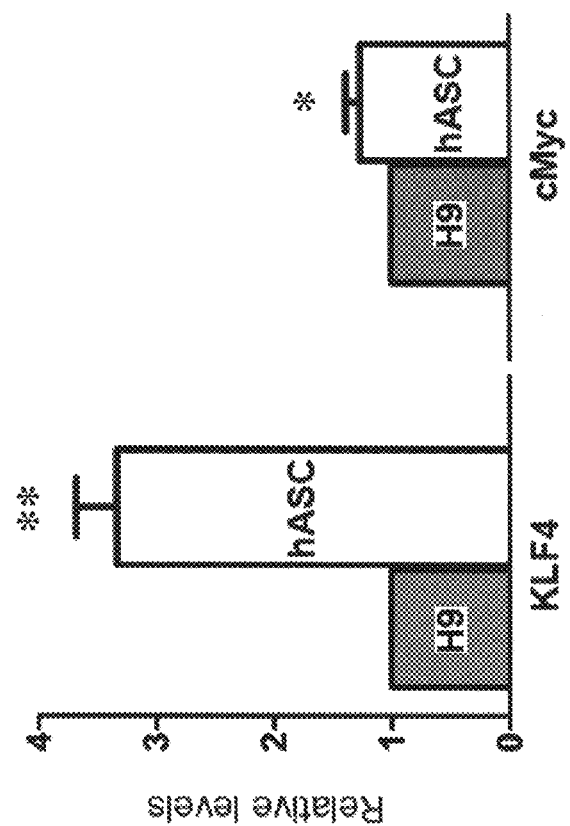
FIG. 5. The relative expression of Klf4 and c-Myc are higher in hASCs compared to H9 human ES cells, as detected by quantitative PCR. 18S was used as housekeeping gene. Data are from three biological replicate experiments. * $p<0.05$ compared to H9, ** $p<0.01$ compared to H9. The error bars represent the standard deviation from three independent experiments.

Minicircle DNA is shown herein to represent an ideal mechanism for generating iPS cells. We constructed a plasmid (P2PhiC31-LGNSO) that contained a single cassette of four reprogramming factors (Oct4, Sox2, Lin28, Nanog) plus a green fluorescent protein (GFP) reporter gene, each separated by self-cleavage peptide 2A sequences. (FIG. 3 a,b). We next took advantage of the PhiC31-based intramolecular recombination system that allows the plasmid backbone to be excluded and degraded in bacteria, and the minicircle to be purified and isolated as described by Chen et al. Molecular Therapy 8, 495-500 (2003); and Chen et al. Human Gene Therapy 16, 126-131 (2005), (FIG. 3c). Expression of individual protein factors was validated in 293FT cells (FIG. 4). To determine the reprogramming ability of the minicircle vector, we chose to induce pluripotency in human adipose stem cells (hASCs). hASCs have a number of advantages over other somatic cell types such as fibroblasts since they can be isolated in large quantities (100 ml of human adipose tissue yields about $1\times10^6$ cells) with minimal morbidity. Furthermore, quantitative PCR (qPCR) of hASCs revealed 3-4 times higher relative expression of Klf4 compared to human ES cells, and ~1.3 higher relative expression of c-Myc (FIG. 5).

Figure 6:
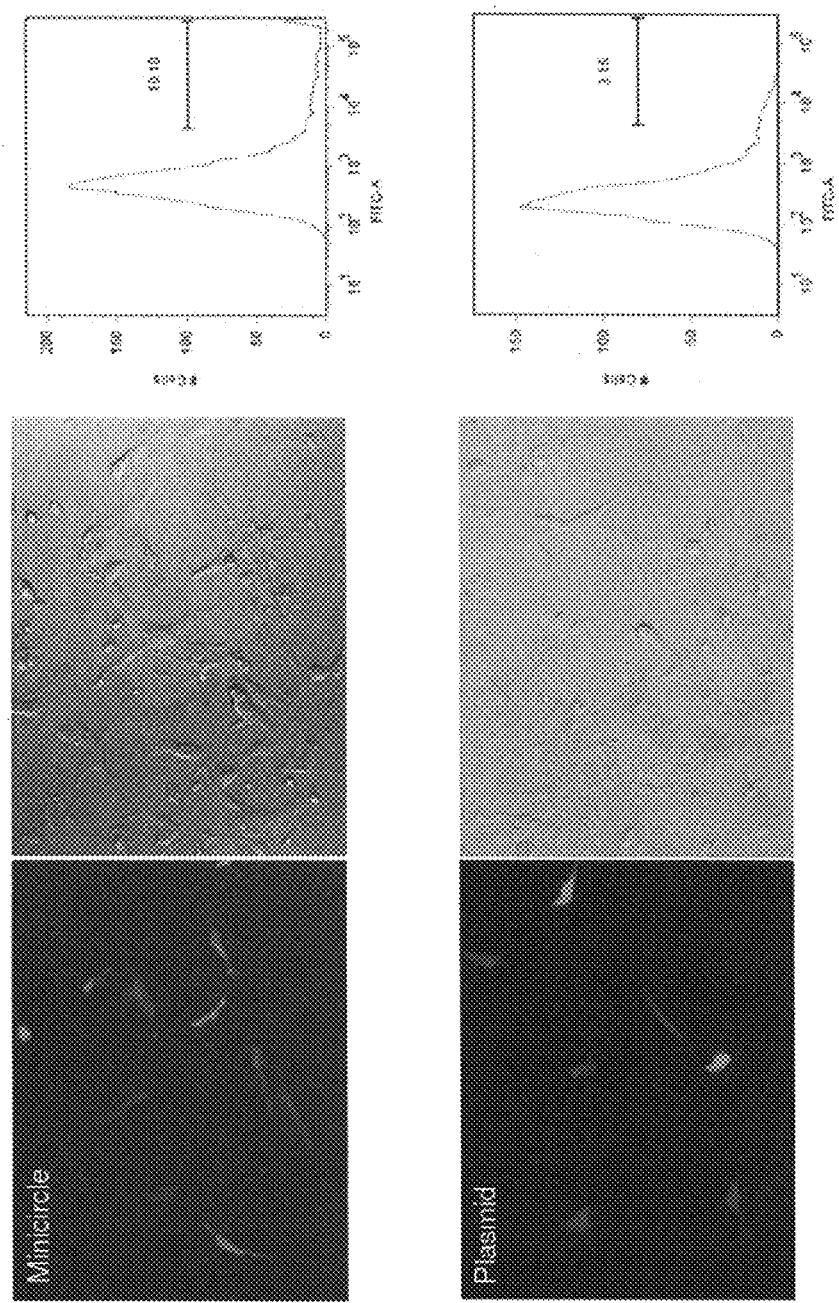
FIG. 6. Using nucleofection, minicircle DNA transfects hASCs more efficiently compared to regular plasmid (10.8±1.7% vs. 2.7±0.8%) as analyzed by flow cytometry 48 hours after transfection. Both minicircle and plasmid vectors contained identical reprogramming factor plus GFP expression cassettes. Representative data from 1 (of 3) independent experiments is shown.
Figure 7:
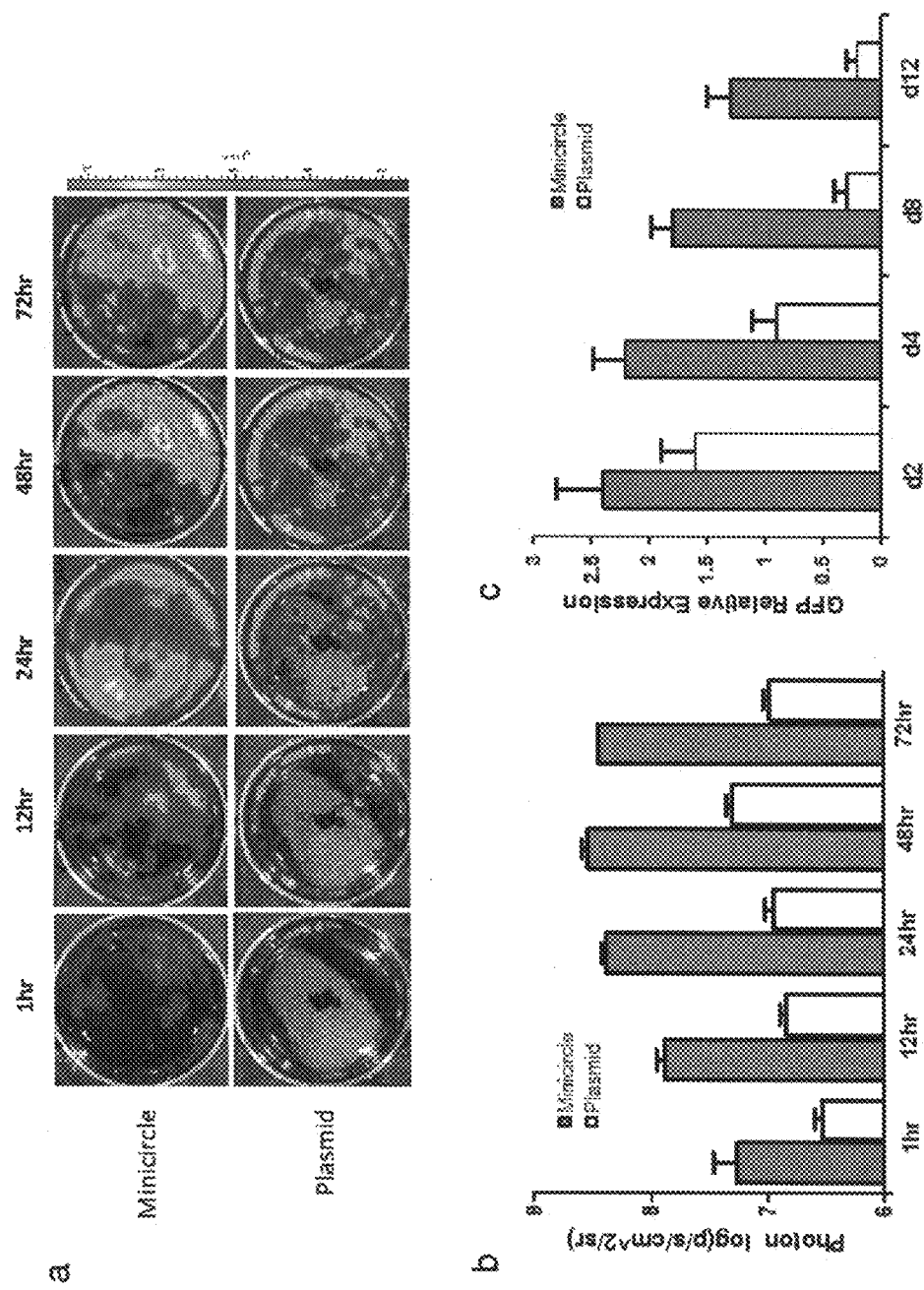
FIG. 7. Minicircle DNA gives stronger and more persistent expression compared to regular plasmid. a, hASCs were transfected with either minicircle or regular plasmid that carried the same expression cassette (CMV-driven, double-fusion GFP-firefly luciferase reporter gene). Shown here are representative bioluminescent images after transfection of in vitro cell cultures at the indicated time points. b, Quantitative photon counts demonstrate increased luciferase expression in minicircle-transfected cells compared to regular plasmid over 72 hrs. c, Quantitative PCR for GFP shows continued higher expression of the minicircle transgene compared to regular plasmid over 12 days. For both experiments, the error bars represent the standard deviation from three independent experiments.

Using hASCs derived from three individual patients, we introduced the minicircle vector into cells using nucleofection and achieved 10.8±1.7% GFP-positive cells, compared to only 2.7±0.8% using a standard plasmid carrying the same expression cassette (FIG. 6). The GFP-positive cell population was enriched 72 h post-transfection by flow cytometry, and then seeded on inactivated mouse embryonic fibroblast (MEF) feeder layers. Due to the dilution of minicircle vector with proliferation, we observed gradual loss of GFP expression in cells. Additional transfections at days 4 and 6 with the minicircle vector were performed to supplement this loss of transgene expression. Importantly, compared to standard plasmids that carry a GFP/firefly luciferase reporter gene, minicircle DNA with the same reporter gene maintains higher expression for a longer period of time in hASCs, as confirmed by photon counts and qPCR (FIG. 7). Thus, minicircle DNA is a more robust gene expression platform compared to regular plasmid.

Figure 2:
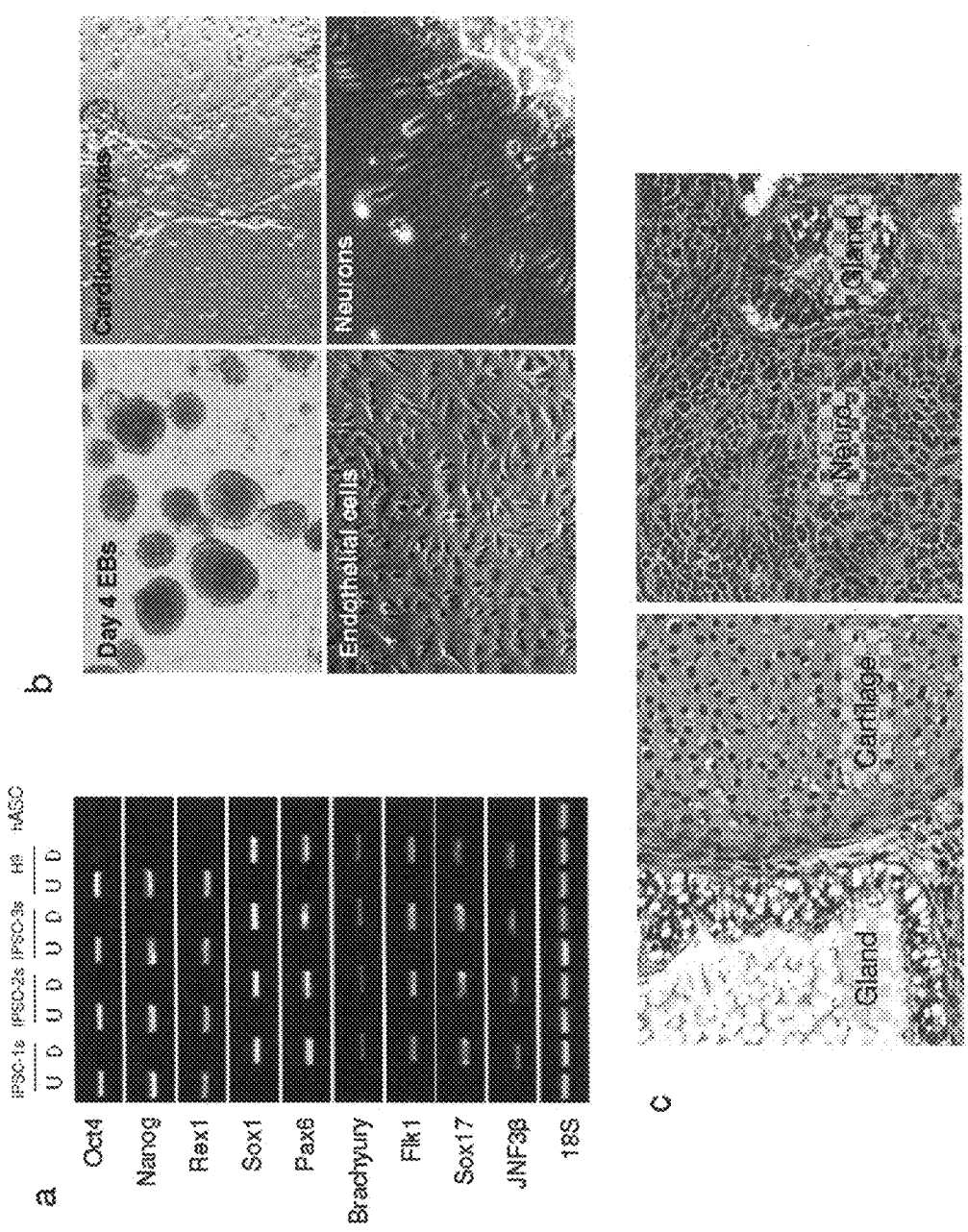
FIG. 2. Pluripotency of mc-iPS cells. a, RT-PCR analysis of pluripotent markers (Oct4, Nanog and Rex1) and various differentiation markers for the three germ layers (ectoderm: Sox1, Pax6; mesoderm: Brachyury, Flk1; endoderm: Sox17, JNF3β). Undifferentiated (U) mc-iPS cells; differentiated (D) mc-iPS cells after 8 days suspension culture followed by 8 days adherent culture. b, Multiple cell types were differentiated from mc-iPS cells. See Supplementary FIG. 7 and Supplementary Video 1 for further characterization. c, Subcutaneous injection of mc-iPS cells causes teratomas in SCID mice consisting of all three embryonic germ layers, including epithelial cells (ectoderm), cartilage (mesoderm), and glandular structures (endoderm). Tissue sections from subclone mc-iPSC-1s are shown as representative.
Figure 8:
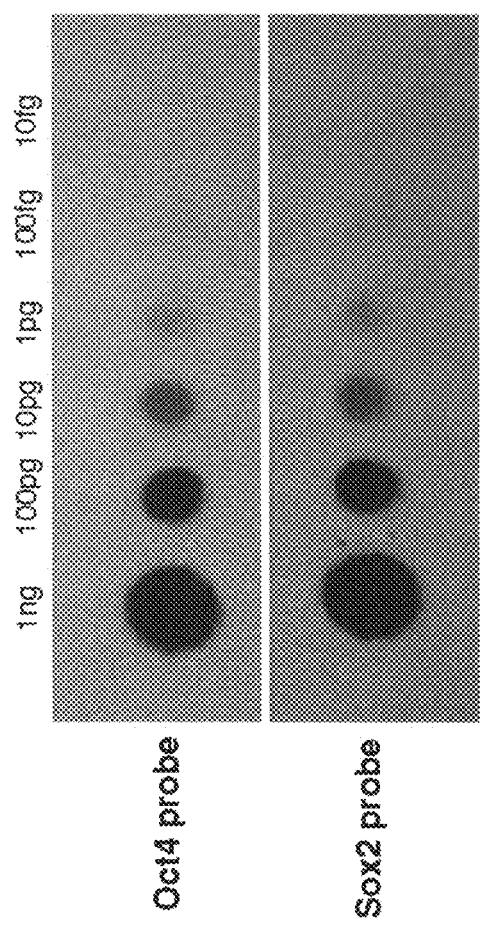
FIG. 8. Sensitivity of Oct4 and Sox2 probes used in Southern blot. Shown are serial dilutions of biotinylated DNA probes that were spotted on BrightStar*-Plus nylon membranes (Ambion). Detection of minicircle DNA was performed according to the manufacturer's protocol. These results demonstrate that the sensitivity limit is ~1 pg for both probes.
Figure 9:
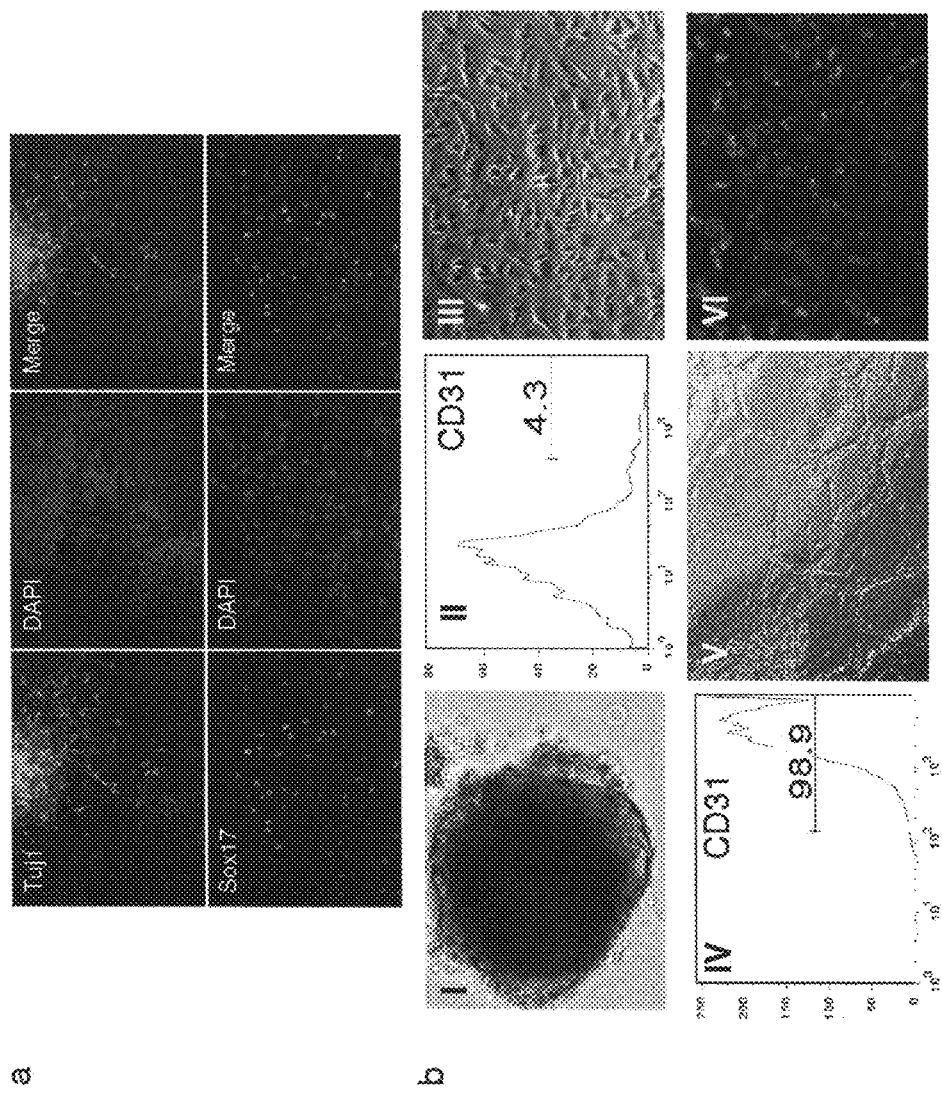
FIG. 9. In vitro differentiation of mc-iPS cells. a, Differentiation into neural progenitors, as indicated by the neuron-specific markers Tuj1 and Sox17. b, Differentiation into endothelial cells. (I, II) At day 12, EBs were collected and digested by Liberase Blendzyme IV and $CD31^+$ cells were isolated by flow sorting. (III, IV) $CD31^+$ cells were sub-cultured in EGM-2 medium (Clonetics) to expand and induce endothelial maturation. FACS analysis shows a majority of cells express CD31. (V) Endothelial tube formation after 12 hours of plating on Matrigel in 24-well plates. (VI) Uptake of Dil-acetylated-LDL (red) by iPS cell-derived endothelial cells. Images are representative of three independent experiments.

On days 14-16, we observed GFP-positive clusters that had morphologic similarities with human ES cell colonies (FIG. 1a). Many clusters showed no GFP expression at all, suggesting loss of transgene expression, and these were isolated for further analysis. Minicircle-derived iPS cell (mc-iPS cell) colonies stained positive for embryonic markers (FIG. 1b,c), and exhibited reactivation of endogenous Oct4, Sox2, and Nanog genes (FIG. 1d,e). Global gene expression profiling of two mc-iPS cell subclones demonstrated a high degree of similarity with human ES cells (FIG. 1f). Importantly, Southern blot analysis did not detect genomic integration of the minicircle transgene in the subclones (FIG. 1g, see FIG. 8 for probe sensitivities). Finally, mc-iPS cells had normal diploid karyotype (FIG. 1h). The pluripotency of mc-iPS cells was examined both in vitro through the formation of embryoid bodies (EBs), and in vivo by teratoma formation. EBs expressed genes of all three embryonic germ layers (FIG. 2a) and formed multi-lineage cell types (FIG. 2b, FIG. 9). Lastly, subcutaneous injection of each of the three mc-iPS subclones into immunodeficient mice resulted in a teratoma (FIG. 2c).

TABLE 1

Estimation of reprogramming efficiency

| Donor | Transfected cells* | Number of human ES cell-like colonies | Efficiency |
|---|---|---|---|
| 1 | $0.9 \times 10^5$ | 4 | 0.004% |
| 2 | $0.6 \times 10^5$ | 3 | 0.005% |
| 3 | $2.4 \times 10^5$ | 15 | 0.006% |

*Transfected cells were collected by sorting GFP+ cells.

In total, we successfully derived 22 mc-iPS cell colonies from hASCs that had been isolated from three individual donors (Table 1), yielding an overall reprogramming efficiency of ~0.005% with minicircle DNA. As with other integration-free iPS cell generation approaches, this efficiency is low compared to viral-based methods, which have typically been reported to be ~0.01%. Our efficiency with minicircle DNA was higher than previous plasmid-based transfection reprogramming methods. We also transfected IMR90 fetal fibroblast with a minicircle vector expressing the four Yamanaka factors (Oct4, Sox2, c-Myc, Klf4), and were able to create iPS cells with similar, though slightly diminished, reprogramming efficiency compared to hASCs reprogrammed with the four Thomson factors. Notably, we were unable to generate iPS cells using regular plasmid vectors expressing all 4 Yamanaka or Thomson factors. We believe this is due to the higher transfection efficiency, and stronger and more persistent expression, of minicircle DNA in cell cultures.

As the reprogramming field moves from basic science towards clinical translation, efficient derivation of iPS cells that are free of foreign or chemical elements is absolutely critical. Here, we describe a simple method for generating transgene-free iPS cells that requires only a single vector without the need for subsequent drug selection or vector-excision. With its basic molecular principles and straightforward protocol, minicircle DNA is ideally suited for facilitating iPS cell research around the world. Finally, the minicircle DNA is already FDA approved, giving this novel method the potential for significant clinical translation.

Materials and Methods

Construction of minicircle DNA vector. The sequences of primers used for plasmid construction are listed in Table 2. The cDNAs for human Oct4, Sox2, Nanog, and Lin28 open reading frames (ORFs) were obtained from human H9 cell line cDNA by PCR. The GFP cDNA ORF was cloned from plasmid pmaxGFP (Amaxa). The Nanog ORF plus T2A adaptable to EcoRI/BglII, the Sox2 ORF plus T2A adaptable to BamHI/XhoI, and the Oct4 ORF adaptable to SalI/XbaI fragments, were separately amplified by PCR and digested with restriction enzymes. The restricted fragments were co-ligated and cloned into a modified pUC vector between EcoRI/XbaI sites. The fragment GFP ORF plus T2A-atgagtgt adaptable to NotI/EcoRI was amplified by PCR and cloned into the vector, as was the Lin28 ORF plus T2A adaptable to SalI/EcoRI. The final vector was designated as pUC-LGNSO, an acronym for the 5 ORFs.

We modified the P2PhiC31 plasmid by introducing CMV promoter and SV40 polyA elements through the following steps. CMV promoter was amplified by PCR and adapted to 5'SalI-3'XhoI NotI, while SV40 polyA element was amplified by PCR and adapted to 5'NotI SpeI-3'XbaI. Both fragments were then co-ligated and cloned into P2PhiC31 between XhoI and SpeI sites, thus establishing a cloning vector with the required expression elements and XhoI/SpeI cloning sites. Subsequently, the LGNSO cassette was retrieved by SalI/XbaI digestion and shuttled into the modified PsPhiC31 plasmid at the XhoI/SpeI sites, creating P2PhiC31 LGNSO plasmid for minicircle-based reprogramming. The minicircle vector was then purified and isolated as described.

TABLE 2

Primers used for vector construction

| SalI 5'Oct4 | GCTGTCGACATGGCGGGACACCTGGCTTCG SEQ ID NO: 1 |
|---|---|
| XbaI 3'Oct4 | CTGTCTAGAACCTTCCCTCCAACCAGTTGC SEQ ID NO: 2 |
| BamHI 5'Sox2 | GAGGGATCCATGTACAACATGATGGAGACGGA SEQ ID NO: 3 |
| XhoI T2A 3'Sox2 | CAGCTCGAGAGGGCCGGGATTCTCCTCCACGT CACCGCATGTTAGAAGACTTCCTCTGCCCTCC ATGTGTGAGAGG SEQ ID NO: 4 |
| EcoRI 5'Nanog | CCTGAATTCATGAGTGTGGATCCAGCTTGT SEQ ID NO: 5 |
| Bgl2 T2A 3' Nanog | CAGAGATCTAGGGCCGGGATTCTCCTCCACGT CACCGCATGTTAGAAGACTTCCTCTGCCCTCT CTCACGTCTTCAGG SEQ ID NO: 6 |
| NheI 5'Lin28 | CAGGCTAGCTTCTTCTCCGAACCAACCC SEQ ID NO: 7 |
| NotI T2A 3'Lin28 | AAGGCGGCCGCAGGGCCGGGATTCTCCTCCAC GTCACCGCATGTTAGAAGACTTCCTCTGCCCT CACCGGTATTCTGTGCCT SEQ ID NO: 8 |
| NotI 5'GFP | GATGCGGCCGCCACCATGGTGAGCAAGGGCGA GGA SEQ ID NO: 9 |
| EcoRI T2A 3'GFP | CATGAATTCAGGGCCGGGATTCTCCTCCACGT CACCGCATGTTAGAAGACTTCCTCTGCCCTCG GCGAAGGCGATGG SEQ ID NO: 10 |

TABLE 2-continued

Primers used for vector construction

| | | |
|---|---|---|
| SalI 5'CMVp | CATGTCGACGTTATTAATAGTAATCAATTACG SEQ ID NO: 11 | |
| NotI XhoI 3'CMVp | ATTGCGGCCGCTCTCGAGCTTGGGTCTCCCTA TAGTGAGTC SEQ ID NO: 12 | |
| NotI SpeI 5'SV40pA | TATGCGGCCGCGACTAGTGAATTCCCGTTGTT TTGCAAATGA SEQ ID NO: 13 | |
| XbaI 3'SV40pA | TCATCTAGATACATTGATGAGTTTGGACA SEQ ID NO: 14 | |

Derivation of human adipose stem cells (hASCs). The phenotype and other characteristics of hASCs have been previously described. hASCs were obtained by lipoaspiration after acquiring informed consent from patients, in accordance with Stanford University human IRB guidelines. All suction assisted lipoaspiration procedures were performed using the VASER Lipo System (Sound Surgical Technologies). hASCs were harvested from the adipose tissue of male or female patients between the ages of 40 and 65 undergoing elective lipoaspiration. Participating patients had no prior knowledge or evidence of ongoing systemic disease at the time of operation. All specimens were immediately placed on ice and were washed sequentially in serial dilutions of dilute Betadine, followed by two phosphate buffered saline (PBS) washes of equal volume. Adipose tissues were subsequently digested with an equal volume of 0.075% (w/v) Type II collagenase in Hank's Balanced Salt Solution at 37° C. in water bath with agitation at 125 rpm for 30 min. After inactivation of collagenase with serum, the stromal vascular fraction was pelleted via centrifugation at 1200 g for 5 min. The cell pellet was resuspended and filtered through a 100 µm cell strainer and the collected cells were plated on 15 cm dishes for further expansion.

Culture and, maintenance of hASCs and mc-iPS cells. hASCs were maintained with Dulbecco's Modified Eagle Medium (DMEM) containing 10% fetal bovine serum (FBS), Glutamax-I, 4.5 g/L glucose, 110 mg/L sodium pyruvate, 50 units/ml penicillin and 50 µg/ml streptomycin at 37° C., 95% air and 5% CO2 in a humidified incubator. All cells used for reprogramming were within passage 2. Derived mc-iPS cells were maintained either on MEF feeder layer or on Matrigel-coated tissue culture dishes (ES qualified, BD Biosciences) with mTESR-1 human ES Growth Medium (StemCell Technologies).

Reprogramming hASCs. Nucleofector Kit R (Amaxa) and program U-023 were used for nucleofection according to the manufacturer's instructions. Transfected hASCs were plated on 10-cm dishes and cultured in DMEM/F12 medium supplemented with 10% FBS. GFP+ cells were sorted by flow cytometry 3 days after transfection. The sorted cells were then seeded on gelatin-coated 6-well plates at ~0.5×10$^5$ cells per well. Cells were switched to human ES cell culture medium 1 day after seeding, as has been previously suggested. Culture medium was refreshed every 2-3 days. On days 4 and 6, we transfected the hASCs again with minicircle using Lipofectamine 2000 (Invitrogen), which we found to be less toxic to cells than nucleofection. Colonies with morphologies similar to human ES cell colonies were clearly visible by day 18 after transfection. At day 26-28 post-transfection, mc-iPS cell colonies were individually picked for further expansion and analysis. For control experiments using regular plasmid, we used the pUC-LGNSO vector and performed all transfections in parallel with minicircle DNA.

Western blot and immunofluorescence. To examine the co-expression of Lin28, Nanog, Sox2, and Oct4, minicircle DNA LGNSO were transfected into 293FT cells with Neofectin (Mid-Atlantic Biolabs). Cells were collected for either Western blot or immunofluorescence analysis two days after transfection. The following primary antibodies were used: rabbit anti-Oct4 (Santa Cruz), rabbit anti-Sox2 (Biolegend), rabbit anti-Nanog (Cosmo Bio), rabbit anti-Lin28 (Proteintech), and mouse anti-GAPDH (Millipore). Antibodies against human ES cell surface markers SSEA4, Tra-1-60, and Tra-1-81 were obtained from ES Cell Characterization Kit (Chemicon). Alexa Fluor-488 and -596 fluorochrome-conjugated secondary antibodies (Molecular Probes) were used for immunofluorescence analysis. Alkaline Phosphatase Detection Kit (Chemicon) was used for alkaline phosphatase staining.

RT-PCR analysis. Total RNA was prepared using RNeasy Mini Kit (Qiagen) and cDNA synthesized with SuperScript™ II First-Strand Synthesis System for RT-PCR (Invitrogen). PCR reactions were performed with Taq DNA polymerase (Qiagen). All primer sequences are listed in Table 3. Note that endogenous genes were measured using 3'-untranslated region specific primers. Quantitative PCR was performed using Taqman Gene Expression Assays (Applied Biosystems) using a StepOnePlus Realtime-PCR System (Applied Biosystems).

TABLE 3

Primers used for RT-PCR analysis

| | | |
|---|---|---|
| Oct4 | 352F | ACCCCTGGTGCCGTGAA SEQ ID NO: 15 |
| | 541R | GGCTGAATACCTTCCCAAATA SEQ ID NO: 16 |
| Oct4 endo* | 912F | GCGATCAAGCAGCGACTA SEQ ID NO: 17 |
| | 1311R | TTCACCTTCCCTCCAACC SEQ ID NO: 18 |
| Sox2 | 890F | CAGCGCATGGACAGTTAC SEQ ID NO: 19 |
| | 1210R | GGAGTGGGAGGAAGAGGT SEQ ID NO: 20 |
| Sox2 endo* | 1183F | CCCTGTGGTTACCTCTTCC SEQ ID NO: 21 |
| | 1441R | CTCCCATTTCCCTCGTTT SEQ ID NO: 22 |
| Nanog | 433F | AAAGGCAAACAACCCACT SEQ ID NO: 23 |
| | 702R | GCTATTCTTCGGCCAGTT SEQ ID NO: 24 |
| Nanog endo* | 1197F | CTCCTCCCATCCCTCATA SEQ ID NO: 25 |
| | 1302R | AGGCTCCAACCATACTCC SEQ ID NO: 26 |
| Lin28 | 270F | GTTCGGCTTCCTGTCCAT SEQ ID NO: 27 |
| | 391R | CTGCCTCACCCTCCTTCA SEQ ID NO: 28 |
| Lin28 endo* | 1135F | AGCCAAGCCACTACATTC SEQ ID NO: 29 |
| | 1434R | AGATACGTCATTCGCACA SEQ ID NO: 30 |
| Eras | F | GCCCCTCATCAGATCCAGATTT SEQ ID NO: 31 |

TABLE 3-continued

Primers used for RT-PCR analysis

| | | |
|---|---|---|
| | R | GCAGCTCAAGGAAGAGGTGT SEQ ID NO: 32 |
| Ecat1 | F | GGCGAGCTGAGATTTGGATA SEQ ID NO: 33 |
| | R | CCAGCCTCCAGAGCCTCTAT SEQ ID NO: 34 |
| Esg1 | F | ATTCGGGCTAAATGGATGC SEQ ID NO: 35 |
| | R | TAGCTCCAGGGTCTTCATGG SEQ ID NO: 36 |
| Crypto | F | TCCTTCTACGGACGGAACTG SEQ ID NO: 37 |
| | R | AGAAATGCCTGAGGAAAGCA SEQ ID NO: 38 |
| Rex1 | F | GGAAGAAATGCTGAAGGTGGAGAC SEQ ID NO: 39 |
| | R | AGTCCCCATCCCCTTCAATAGC SEQ ID NO: 40 |
| Sox1 | F | CACAACTCGGAGATCAGCAA SEQ ID NO: 41 |
| | R | GGTACTTGTAATCCGGGTGC SEQ ID NO: 42 |
| Pax2 | F | GTCCATCTTTGCTTGGGAAA SEQ ID NO: 43 |
| | R | TAGCCAGGTTGCGAAGAACT SEQ ID NO: 44 |
| Brachyury | F | AATTGGTCCAGCCTTGGAAT SEQ ID NO: 45 |
| | R | CGTTGCTCACAGACCACA SEQ ID NO: 46 |
| Flk1 | F | TGATCGGAAATGACACTGGA SEQ ID NO: 47 |
| | R | CACGACTCCATGTTGGTCAC SEQ ID NO: 48 |
| Sox17 | F | CTCTGCCTCCTCCACGAA SEQ ID NO: 49 |
| | R | CAGAATCCAGACCTGCACAA SEQ ID NO: 50 |
| HNF3β | F | GGAGCGGTGAAGATGGAA SEQ ID NO: 51 |
| | R | TACGTGTTCATGCCGTTCAT SEQ ID NO: 52 |

*primers specifically recognize endogenous gene.

Southern blotting. 10 µg of genomic DNA was isolated and digested with EcoRI from mc-iPS cell subclones derived from each of the three human donors, hASCs, and H9 human ES cells. As positive-controls, we included human iPS cells derived using lentiviral transduction methods (courtesy Dr. James Thomson, U. of Wisconsin), as well as EcoRI-digested and undigested minicircle DNA (8.8 pg starting amounts). After digestion, DNA was separated in 0.8% agarose gel in TAE buffer, then capillary-transferred overnight onto a positively charged BrightStar™-Plus nylon membrane (Ambion) in alkaline solution (0.4 N NaOH, 1 M NaCl). Hybridization was performed using synthesized biotin-labeled probes for either Oct4 or Sox2, and detected with the Biostar-BioDetected™ Kit (Ambion).

Bisulfite pyrosequencing. We used a service provider (EpigenDx). Briefly, 1000 ng of sample DNA was bisulfate treated using the Zymo DNA Methylation Kit (Zymo Research). The PCR was then performed with one of the PCR primers biotinylated to convert the PCR product to single-stranded DNA templates. The PCR products were sequenced by Pyrosequencing PSQ96 HS System (Biotage) following the manufacturer's instructions (Biotage). The methylation status of each locus was analyzed individually as a TIC SNP using QCpG software (Biotage).

Microarray hybridization and data acquisition. Total RNA was prepared from biological duplicate samples of hASCs and H7 human ES cells, and mc-iPS cell subclones from two individuals, for a total of 6 unique samples. Using Agilent Low RNA Input Fluorescent Linear Amplification Kits, cDNA was reverse transcribed from each RNA sample, as well as from a pooled reference control, and cRNA then transcribed and fluorescently labeled with Cy5/Cy3. cRNA was purified using an RNeasy kit (Qiagen). 825 ng of Cy3- and Cy5-labeled and amplified cRNA was hybridized to Agilent 4×44K whole human genome microarrays (G4112F) and processed according to the manufacturer's instructions. The array was scanned using an Agilent G2505B DNA microarray scanner. The image files were extracted using Agilent Feature Extraction software version 9.5.1 applying LOWESS background subtraction and dye-normalization. The data were analyzed using GeneSpring GX 10.0 (Agilent Technologies, Santa Clara, Calif.). For heatmap generation, we used ANOVA statistical analysis with multiple testing correction to identify genes which had significant ($P<0.01$) changed expression between each group; the fold change data for hASC and H7 human ES cell duplicate samples were averaged for the heatmap. For hierarchical clustering, we used Pearson correlation for similarity measure and average linkage clustering.

Flow cytometry analysis and sorting. FACS analysis and sorting was carried out using a BD LSR analyzer (BD Biosciences) or FACSVantage SE Flow Cytometry System (BD Biosciences) at the Stanford Shared FACS Facility, and data were analyzed by FlowJo (Tree Star Inc). Antibodies used in this study were anti-CD31 (BD Pharmingen) for endothelial cell studies; otherwise cells were sorted by GFP expression. Isotype-matched antibodies were used in flow cytometry for background fluorescence.

Bioluminescence imaging. We constructed a double-fusion reporter gene plasmid (GFP/firefly luciferase) driven by a CMV promoter, and created a minicircle vector from the expression cassette using the techniques already described. In vitro imaging of minicircle- or plasmid-transfected hASCs (see Supplementary FIG. 5) was performed with the Xenogen In Vivo Imaging System (Caliper LifeSciences). Before imaging, cell media was removed and D-Luciferin (Biosynth AG) and phosphate-buffered saline (PBS) added in a 1:100 ratio. Exposures were taken within 5 minutes of addition of D-Luciferin, and then repeated until maximum bioluminescent signal expressed as photons/sec/cm$^2$/sr was obtained. Three independent experiments were performed.

In vitro differentiation. mc-iPS cells cultured on Matrigel were treated with Collagenase Type IV (Invitrogen) and transferred to ultra-low attachment plates (Corning Life Sciences) in suspension culture for 8 days with DMEM/F12 (1:1) containing 20% knockout serum (Invitrogen), 4.5 g/L L-glutamine, 1% nonessential amino acids, 0.1 mM 2-mercaptoethanol, 50 units/ml penicillin, and 50 µg/ml streptomycin. EBs were then seeded in 0.25% gelatin-coated tissue culture dish for another 8 days. Spontaneous differentiation of mc-iPS cells into cells of mesoderm, endoderm, and ectoderm lineages was then detected by RT-PCR and appropriate markers by immunofluorescence. Directed differentiation of mc-iPS to cardiomyocytes, neurons, and endothelial cells followed previously published protocols.

Teratoma formation. To examine the in vivo developmental potential of human iPS cells generated through minicircle DNA-based reprogramming, mc-iPS cells grown on Matrigel-coated dishes were collected by Collagenase IV treatment and injected into the dorsal flank of 6 week-old immunocompromised SCID-beige mice. We injected $0.5 \times 10^6$ cells from each of the three donor iPS cell lines into individual mice, and repeated the experiment a total of three times (n=9 mice total). After eight weeks, teratomas from all mice were dissected and fixed in 4% paraformaldehyde. Samples were embedded in paraffin and processed with hematoxylin and eosin staining.

Statistical analysis. Unless otherwise noted, non-microarray data are presented as mean±S.D. Data were compared using standard or repeated measures, using ANOVA where appropriate. Pairwise comparisons were performed using a two-tailed Student's t-test. For all data, differences were considered significant for P-values<0.05.

Example 2

Feeder-Free Derivation of Induced Pluripotent Stem Cells from Adult Human Adipose Stem Cells Ectopic expression of transcription factors can reprogram somatic cells to a pluripotent state. However, most of the studies used skin fibroblasts as the starting population for reprogramming, which usually take weeks for expansion from a single biopsy. We show here that induced pluripotent stem (iPS) cells can be generated from adult human adipose stem cells (hASCs) freshly isolated from patients. Furthermore, iPS cells can be readily derived from adult hASCs in a feeder-free condition, thereby eliminating potential variability caused by using feeder cells. hASCs can be safely and readily isolated from adult humans in large quantities without extended time for expansion, are easy to maintain in culture, and therefore represent an ideal autologous source of cells for generating individual-specific iPS cells.

Induced pluripotent stem (iPS) cells have been successfully derived from somatic cells with ectopic expression of transcription factors Oct4, Sox2, and either Klf4 and c-MYC or Nanog and Lin28. More importantly, the generation of patient-specific and disease-specific iPS cells has the potential to greatly impact the future of regenerative medicine, drug development, as well as our basic understanding of specific disease mechanisms. With the fast progress in this field, different reprogramming strategies have been developed, including using nonintegrating adenoviruses, two factors with small molecules, reprogramming with a polycistronic cassette containing all four factors, excisable transposons, and more recently, virus-free plasmid.

However, the majority of these studies use skin fibroblasts as the parental cells, which usually requires at least 4 weeks to expand from a single skin biopsy to get enough starting cells for reprogramming. The reprogramming efficiency of adult human fibroblasts using "Yamanaka" four factors (Oct4, Sox2, Klf4, and c-MYC) is also still very low at under 0.01%. Although Zhao et al. reported improved reprogramming efficiency of adult human fibroblasts using p53 and UTF1 siRNAs, inhibition of p53, a potent tumor suppressor, may cause the reprogrammed iPS cells to be less safe for future application.

Another critical consideration within the iPS cell field is the more practical concern of accessibility of parental cells for reprogramming. In humans, many cell types such as hepatocytes and neural progenitors are not easily accessible without performing highly invasive procedures. Moreover, some sources of cells are rare and not available in large quantities, making them poor candidates for reprogramming in a clinical setting. For example, neural stem cells that can be reprogrammed with only a single factor, Oct4, are a rare population and technically difficult to obtain.

Human adipose stem cells (hASCs) are a heterogeneous group of multipotent progenitor cells that can be readily derived from adipose tissue of adult humans in very large quantities by lipoaspiration. These cells are multipotent stem cells and can differentiate into adipogenic, osteogenic, chondrogenic, and myogenic cell lineages. hASCs may therefore possess a different genetic and epigenetic landscape that is more ideal for reprogramming than the terminally differentiated fibroblast cells.

Here we report that hASCs obtained from four 40- to 65-year-old individuals can be reprogrammed into iPS cells. The appearance of embryonic stem (ES) cell-like colonies from reprogramming hASCs was ~2-fold faster and ~20-fold more efficient than from reprogramming human IMR90 fibroblasts using the Yamanaka four factors. Furthermore, iPS cells can be readily derived from hASCs on feeder-free surfaces using Matrigel-coated tissue culture dishes, thereby reducing the variability of reprogramming processes that may be caused by using mouse feeder cells. Our results indicate that hASCs are an easily obtainable cell source that can be more efficiently reprogrammed into adult, individual-specific iPS cells.

In our reprogramming experiments, we first isolated hASCs via lipoaspiration from four individuals between the ages of 40 and 65. The human fibroblast cell line IMR90 was used in parallel to compare the efficiency and length of time for the reprogramming process. Cells were first transduced with individual lentiviruses containing human Oct4, Sox2, Klf4, and c-MYC at a 1:1:1:1 ratio on day 0. Transduction was repeated on day 2 using the same batch of all four lentiviruses. The efficiency for each lentiviral transduction was greater than 50%. On day 3 after the first transduction, 50,000 cells were transferred onto mouse embryonic fibroblast (MEF) feeder layer, with the culture medium switched from the hASC growth medium to human embryonic stem (hES) cell growth medium mTeSR-1.

Figure 15:
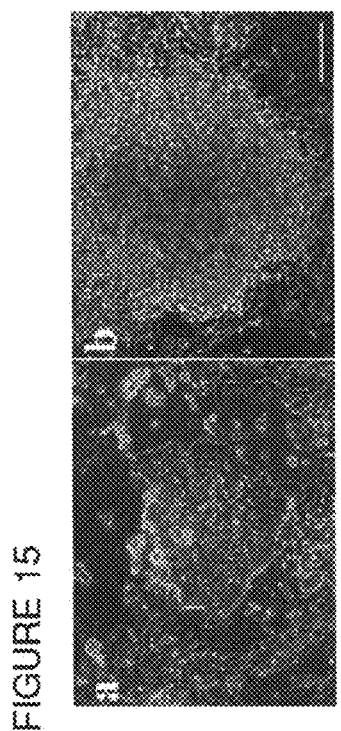
FIG. 15. (a) A typical ES cell-like colony and (b) non-ES cell-like colony derived from reprogramming hASCs on day 12 after transduction. (Scale bar, 100 µm.)

We observed many small colonies of non-ES cell-like cells beginning on day 4 that had morphologies similar to the "background colonies" or "early colonies" described in previous studies. These non-ES cell-like colonies expanded rapidly but lacked the typical characteristics of hES cells, such as defined boundaries and high nuclear-to-cytoplasm ratio within individual cells (FIG. 15). From day 12-13, clearly recognizable, tightly packed colonies with morphologies similar to hES cells appeared.

Figure 16:
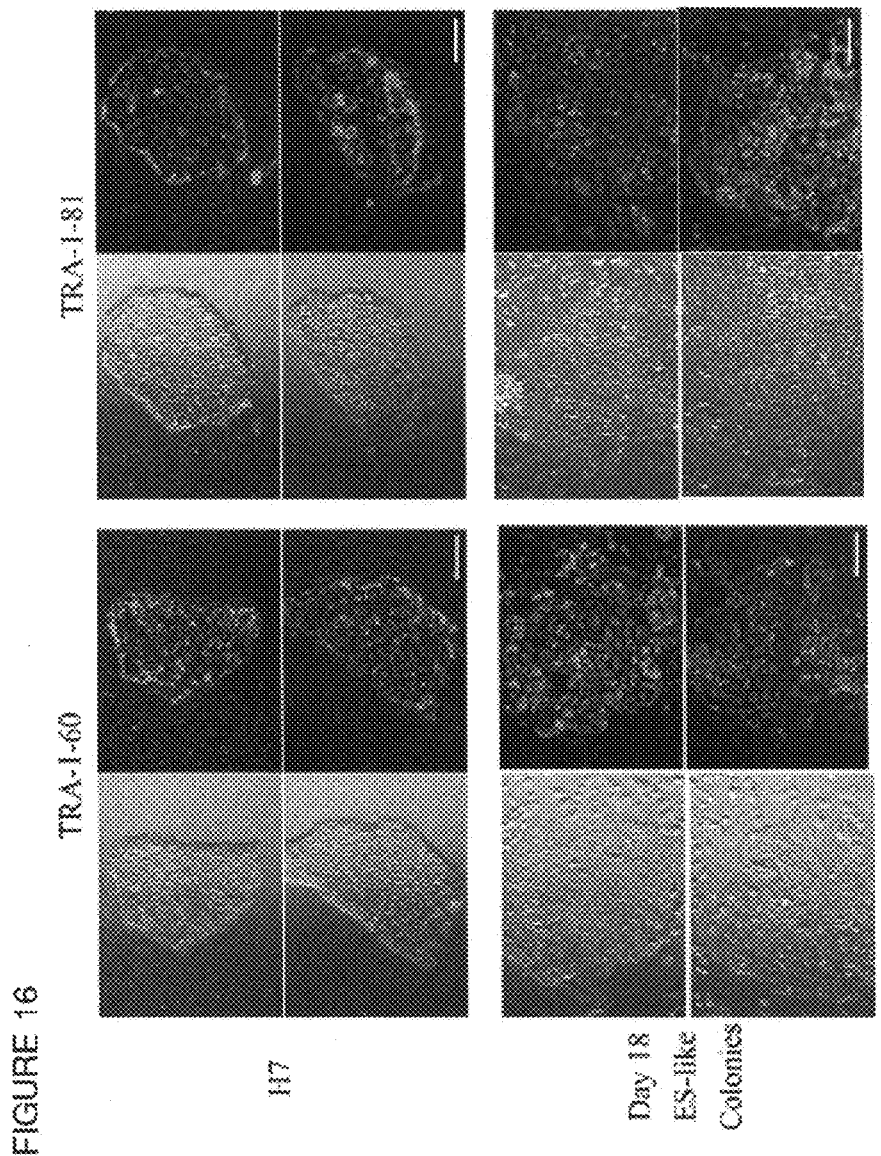
FIG. 16. The staining patterns of TRA-1-60 on hES cells and the ES cell-like putative hASC-iPS colonies were comparable with those of TRA-1-81 immunostaining. Left column, TRA-1-60 immunostaining (green, right panel) of H7 hES cells and the ES cell-like colonies of hASC reprogramming (day 18 after transduction) on Matrigel. Two representative colonies were shown for each cell type, and the left panels were phase images of the colonies. Right column, TRA-1-81 immunostaining (green, right panel) of H7 hES cells and the ES cell-like colonies of hASC reprogramming (day 18 after transduction) on Matrigel. Note that both TRA-1-60 and TRA-1-81 staining were specific for the hES cells or the reprogrammed ES cell-like hASC-iPS colonies and exhibited similar pattern of small dense dots spread on the surface of the cells. The overall appearances of TRA-1-60 and TRA-1-81 immunostaining were also similar for the entire hES cells or the reprogrammed ES cell-like colonies.

Previous studies have reported the isolation of human iPS cells based on both cell morphology and immunostaining of living cells with the embryonic surface marker TRA-1-81. In our study, we compared the immunostaining of the hES cells and the reprogrammed ES cell-like colonies by TRA-1-81 and TRA-1-60, and found that TRA-1-60 showed comparable staining with that of TRA-1-81 for both hES cells and the ES cell-like colonies from reprogramming of hASCs (FIG. 16). TRA-1-60 has also been used in combination with endogenous Nanog expression to determine the success of reprogramming. We thus moved along using TRA-1-60 as the surface marker together with typical ES cell-like morphology to track the progression of the putative iPS colonies. We consistently observed TRA-1-60 positive colonies that appeared as early as on day 10, although these colonies were still too small to be recognized with brightfield microscopy.

The number and size of the TRA-1-60 positive colonies increased over time after day 10. From day 15 to day 16, large ES cell-like colonies containing ~400-500 cells could be isolated mechanically and transferred onto Matrigel for further expansion.

For each hASC line reprogrammed, we consistently observed ~100 TRA-1-60 positive, ES cell-like colonies out of 50,000 cells on day 16 (Tables 4-5).

TABLE 4

Table 1. TRA-1-60-positive ES-like colonies

| Cell line | Day 16 on MEFs (out of 5 × 10⁴ cells) | Day 18 on Matrigel (out of 2 × 10⁵ cells) |
| --- | --- | --- |
| hASC-I1 | 73 ± 12 (n = 6) | 22 ± 5 (n = 5) |
| hASC-I2 | 96 ± 15 (n = 5) | 57 ± 10 (n = 4) |
| hASC-I3 | 110 ± 12 (n = 4) | 40 ± 7 (n = 4) |
| hASC-I4 | 87 ± 7 (n = 4) | 23 ± 4 (n = 3) |
| IMR90 | 2~4 (n = 4) | 0 (n = 6) |

TABLE 5

Table S1. Derivation of hASC-IPS cell lines

| | Individual | Colonies picked | Cell line established | Teratoma tested |
| --- | --- | --- | --- | --- |
| Feeder-Free | 1 | 6 | e | 2 |
| | 2 | 6 | 6 | 2 |
| | 3 | 6 | 5 | 2 |
| | 4 | g | 6 | 2 |
| With Feeder | 1 | 4 | 4 | N |
| | 2 | 4 | 4 | N |
| | 3 | 4 | 4 | N |
| | 4 | 4 | 3 | N |

N—None tested

Figure 17:
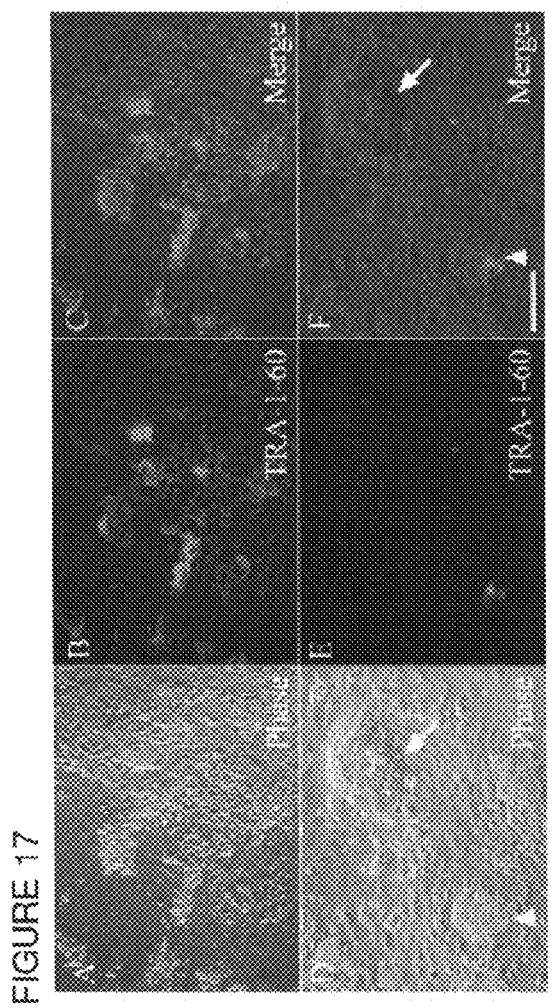
FIG. 17. Non-ES cell-like colonies with background non-specific TRA-1-60 immunofluorescence and ES cell-like colonies negative for TRA-1-60. (A-C), Representative non-ES cell-like colonies with background nonspecific TRA-1-60 immunofluorescence. (D-F), An ES cell-like colony (arrow) negative for TRA-1-60 immunofluorescence and a non-ES cell-like colony (arrow head) with partial background non-specific TRA-1-60 immunofluorescence. (Scale bar, 100 µm.)
Figure 18:
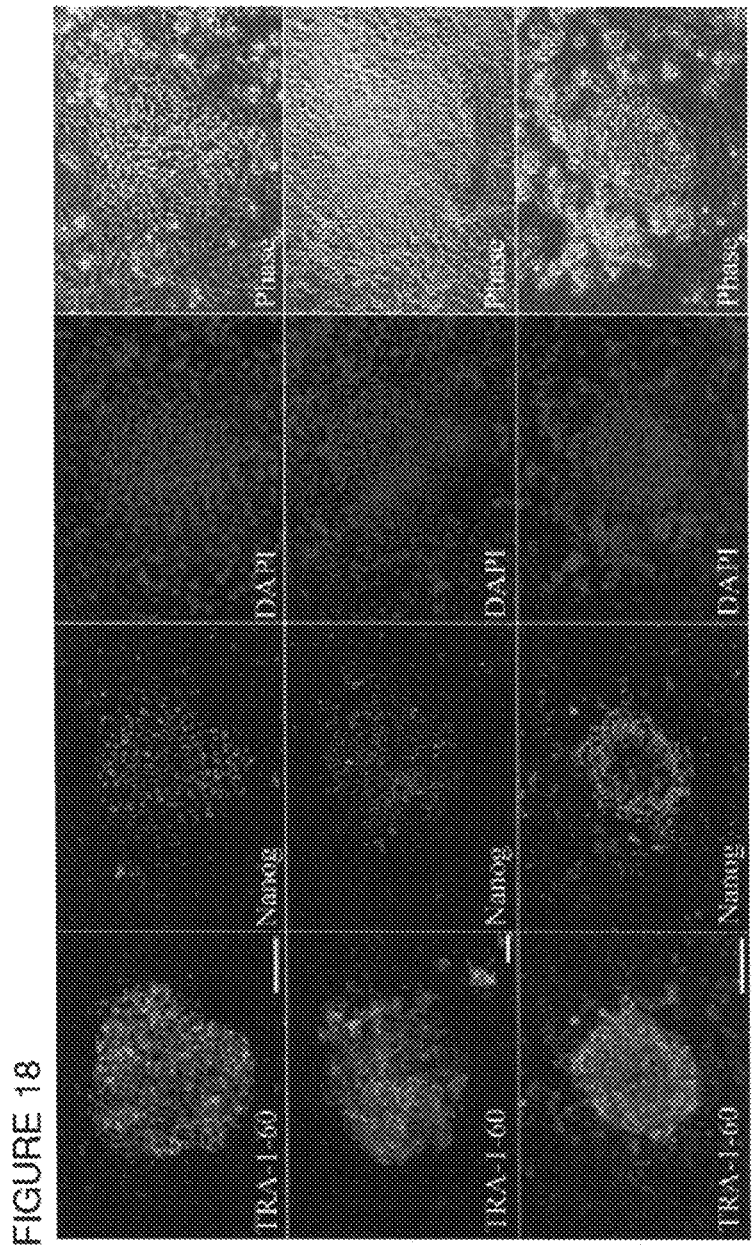
FIG. 18. Immunostaining of TRA-1-60 and endogenous Nanog expression of the ES cell-like colonies appeared day 16-18 posttransduction. Shown are three representative ES cell-like colonies that were positive for TRA-1-60 (green) and Nanog (red). Nuclei were stained blue with DAPI. Note that the phase images of the ES cell-like colonies lost the typical light refractive properties after fixation for immunostaining. (Scale bars, 50 µm.)

The number of non-ES cell-like colonies varied in each reprogramming and was higher than the number of ES cell-like colonies. Some non-ES cell-like colonies overgrew over time and detached from the feeder cells. Previous studies have reported calculating reprogramming efficiency based solely on the ES cell-like morphologies of the observed colonies with a success rate of ~90-100%. However, we did observe a few colonies that had ES cell-like morphologies but were negative for TRA-1-60/TRA-1-81 and some non-ES cell-like cell clumps with nonspecific TRA-1-60/TRA-1-81 staining (FIG. 17). Therefore in this study, we combined the ES cell-like morphology and TRA-1-60 immunostaining of living cells to improve the accuracy of determinations of our reprogramming efficiency. We believe that the combination of TRA-1-60 expression and ES cell-like morphology represents a more rigorous criteria, or at least comparable with previous criteria, for calculating reprogramming efficiency. Indeed, ~90% TRA-1-60 positive ES cell-like colonies that we tested on day 18 posttransduction expressed the late pluripotency marker Nanog (FIG. 18), suggesting a high success rate of identifying reprogrammed colonies. Based on this method, the calculated efficiency of reprogramming was ~0.2%. In contrast, reprogramming IMR90 cells carried out under the same conditions resulted in only approximately two to four recognizable TRA-1-60 positive colonies out of 50,000 cells 28 days after transduction. This low reprogramming efficiency using IMR90 fibroblasts is consistent with and comparable to the results reported by previous studies using Yamanaka four factors to reprogram human fibroblasts. To our knowledge, the highest efficiency of reprogramming adult human fibroblast cells with the Yamanaka four factors described in current literature is only ~0.01%. Based on the appearance and number of TRA-1-60 positive ES cell-like colonies, our results indicate that reprogramming adult hASCs is more efficient and faster than reprogramming adult human fibroblasts.

Figure 10:
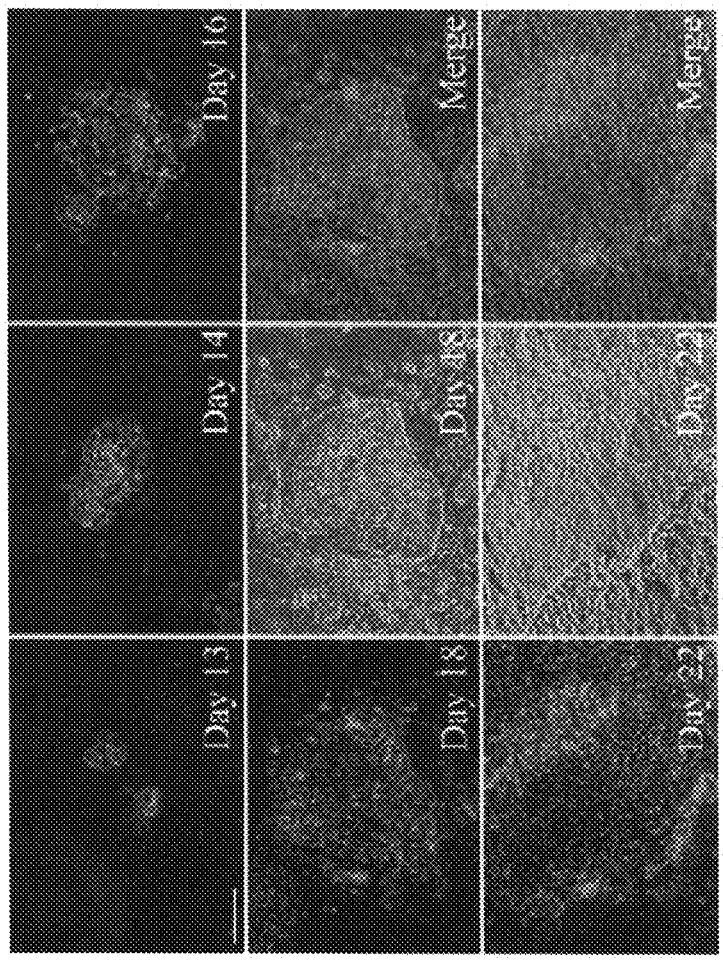
FIG. 10. Tracking the appearance and growth of an ES cell-like colony by immunostaining the living cells with TRA-1-60 in feeder-free reprogramming. Adult hASCs were seeded on Matrigel-coated surface without MEF feeder cells. The living cells were stained repetitively with TRA-1-60 monoclonal antibodies and AlexaFluor 488 secondary antibodies over the indicated period. Day 18 and 22 images are presented both in fluorescent and phase contrast microscopy. Note that TRA-1-60 expression was specific for the ES cell-like colony. (Scale bar, 100 μm.)

We also attempted to generate iPS cells from hASCs under feeder-free conditions. We seeded 2×10⁵ hASCs from each of the four individuals directly on the Matrigel-coated surface within one well of a six-well tissue culture dish and transduced the cells with all four factors. TRA-1-60 positive colonies appeared as early as on day 12. Recognizable TRA-1-60 positive ES cell-like colonies surrounded by cobblestone-like cells originating from hASCs were observed as early as on day ~13-14 under brightfield microscopy. Large TRA-1-60 positive; ES cell-like colonies could be visualized and were transferred to new Matrigel-coated dishes for further expansion from day ~18-20. The developmental progression of a typical ES cell-like colony on Matrigel is shown in FIG. 10. We consistently obtained ~20-70 TRA-1-60 positive ES cell-like colonies (Table 4) out of 2×10⁵ seeded hASCs on Matrigel without feeder cells, which accounts for an efficiency of ~0.01-0.03%. However, the initial density of the seeded cells seemed to be critical for successful reprogramming, because ES cell-like colonies were not observed when less than 1×10⁵ hASCs were initially seeded. Because the hASC derived ES cell-like colonies are morphologically indistinguishable from hES cells, we thus defined them as "hASC-iPS cells."

Figure 11:
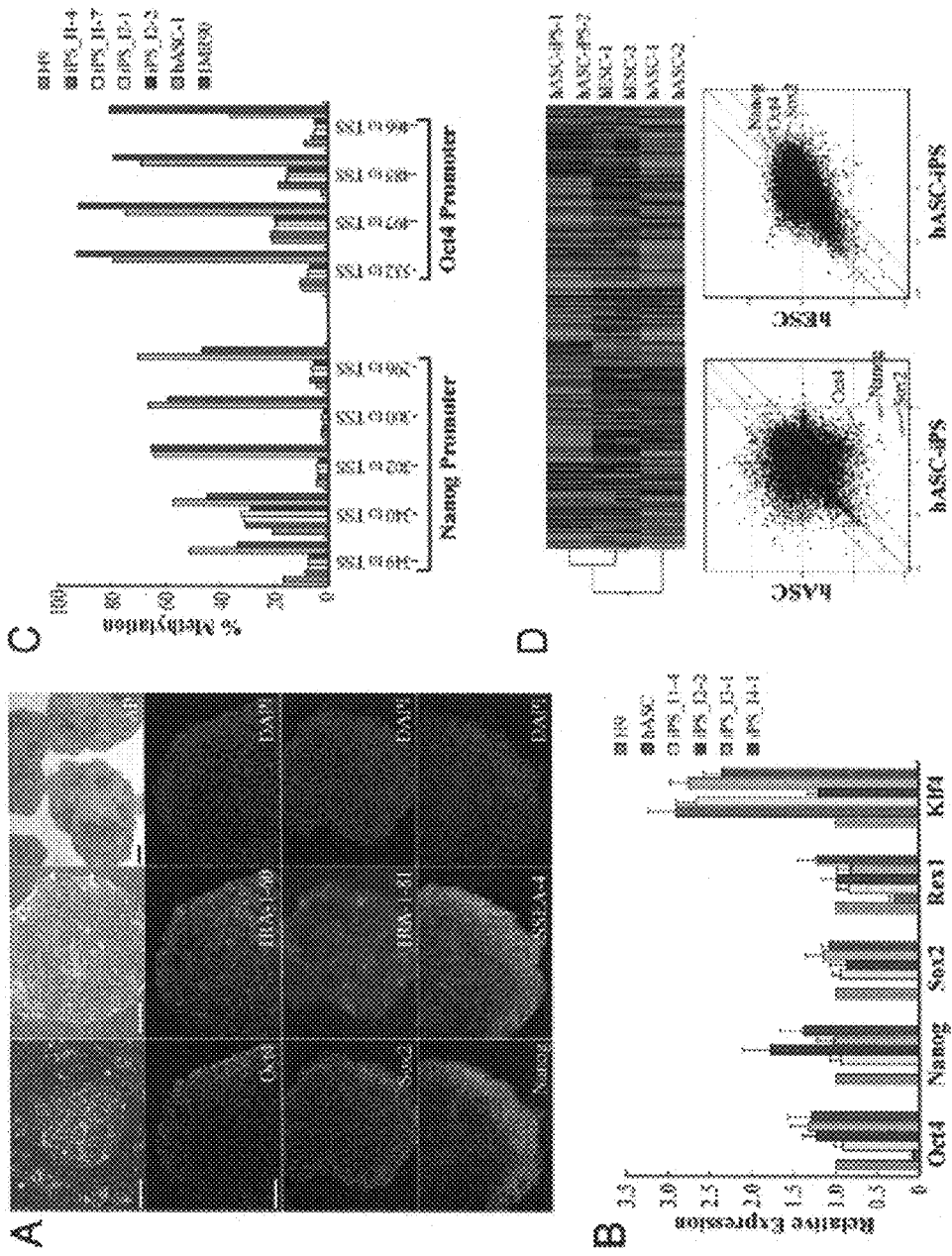
FIG. 11. Characterization of hASC-iPS cells. (A) Immunostaining of hASC-iPS cell colonies with common hES cell markers. The two phase contrast microscopies show a typical hASC-iPS cell colony growing on MEF feeder cells and feeder-free Matrigel surface, respectively. (Scale bars, 100 μm.) (B) Quantitative-PCR analyzing pluripotency gene expression level within hASCs and hASC-iPS cells relative to those in H9 hES cells. iPS_I1-4 denotes iPS cell line #4 derived from individual 1. (C) Bisulphite pyrosequencing measuring methylation status within the promoter region of Oct4 and Nanog genes in H9 hES cells, hASC-iPS cells, hASCs, and IMR90 cells. TSS, transcription start site. (D) Microarray data comparing global gene expression profiles of hASCs, hASC-iPS cells, and hES cells. Upper panel, heat map and hierarchical clustering analysis by Pearson correlation showing hASC-iPS cells are similar to hES cells and distinct from hASCs. Lower panel, scatter plots comparing global gene expression patterns between hASCs, hASC-iPS cells, and hES cells. Highlighted are the pluripotency genes Oct4, Sox2, and Nanog (red arrows). The green diagonal lines indicated linear equivalent and 5-fold changes in gene expression levels between paired samples.
Figure 19:
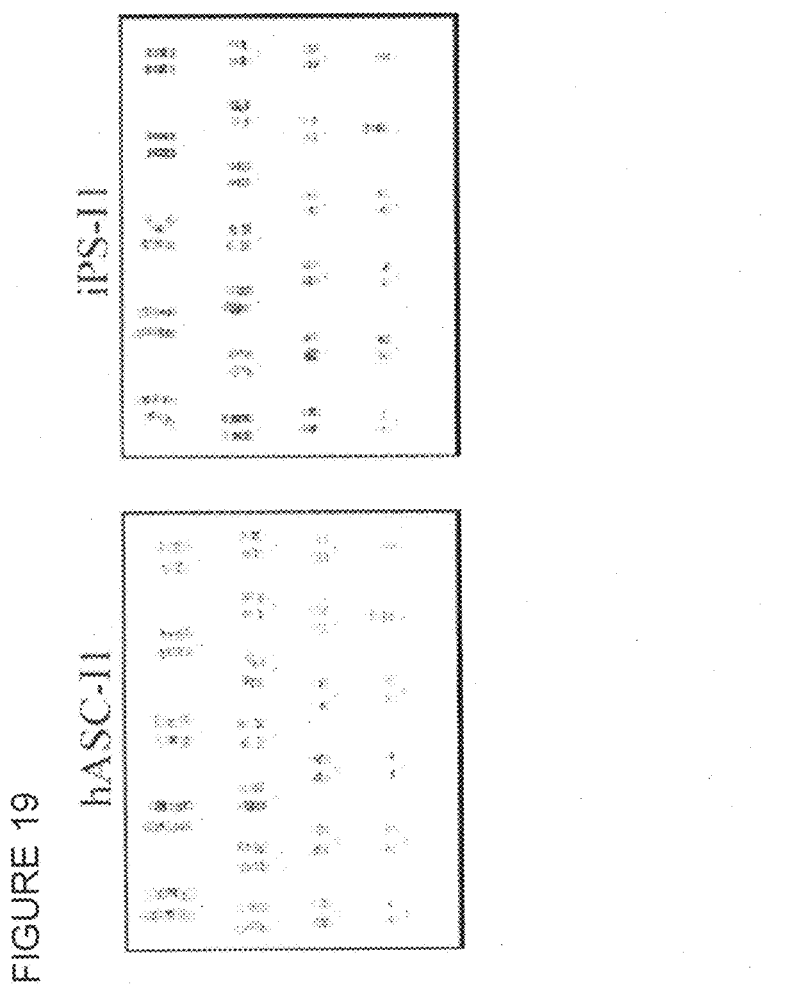
FIG. 19. hASC-iPS cells have a normal karyotype. Representative images showing iPS cells derived from hASCs of individual 1 (I1) have the same normal 46, XY karyotype.

We next characterized the hASC-iPS cells that were isolated from the large ES cell-like TRA-1-60 positive colonies (~>500-600 cells/colony) generated in feeder-free conditions. We chose to use feeder-free hASC-iPS cell lines for further analysis to eliminate the potential contaminating factors from feeder cells and also to ensure that our analysis was consistent among the different cell lines. We initially picked eight single colonies from feeder-free reprogramming hASCs of individual 1, and six out of the eight picked single colonies were successfully expanded in feeder-free culture condition. For individual 2, 3, and 4, we picked six single colonies from each individual. All total 18 colonies, but one was successfully expanded and cultured in feeder-free condition for extended time (Table 5). Immunostaining of different feeder-free hASC-iPS cell lines with alkaline phosphatase (AP), Oct4, Sox2, Nanog, TRA-1-60, TRA-1-81, and SSEA-4 indicated they are positive for typical hES cell markers (FIG. 11A). The expression level of several pluripotency genes in hASC-derived iPS cells was also analyzed by quantitative PCR (FIG. 11B). Of the four lines of hASC-derived iPS cells analyzed, Oct4, Sox2, Nanog, and Rex1 were expressed at comparable levels with those of H9 hES cells. In contrast, nonreprogrammed hASCs showed very low or no expression of these genes. Overall, our results indicate that the pluripotency gene expression level in hASC-derived iPS cells is similar with those in hES cells. Interestingly, the expression level of Klf4, one of the reprogramming factors, was found to be ~3-fold higher in hASCs than in H9 hES cells (FIG. 11B). The hASC-iPS cells also had a normal karyotype after extended culture for 3 months with 46 chromosomes and no translocations (FIG. 19), indicating maintenance of chromosome stability overtime.

The promoter regions of pluripotency genes in reprogrammed somatic cells are often demethylated, causing increased expression of downstream genes. We therefore analyzed the methylation status of the Oct4 and Nanog promoter regions of hASCs and hASC-iPS cells by quantitative bisulphite pyrosequencing. All of the tested hASC-iPS cell lines shared a hypomethylation pattern similar to that of hES cells, whereas hASCs showed prominent methylation at these loci similar to that of IMR90 fibroblasts (FIG. 11C). These results demonstrate epigenetic remodeling of the Oct4 and Nanog promoters within the hASCderived iPS cells and are indicative of successful reprogramming.

Figure 12:
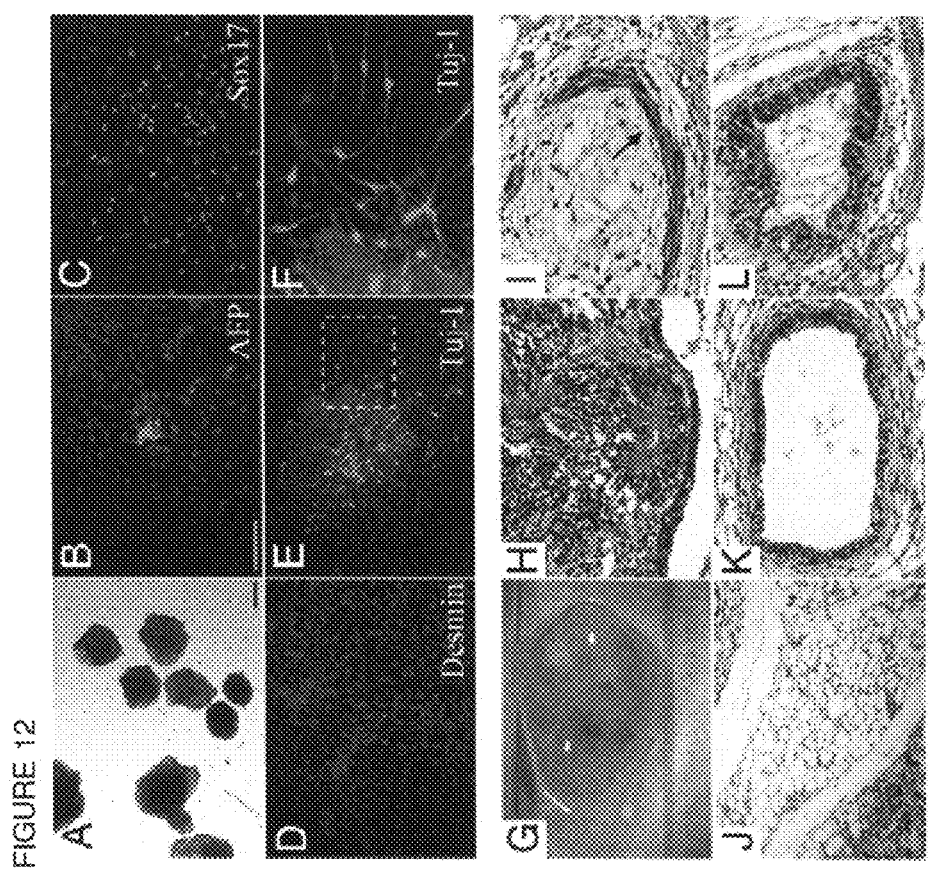
FIG. 12. hASC-iPS cells are pluripotent. (A) hASC-iPS cells form EBs and can differentiate to cells of (8 and C) endoderm [α-fetoprotein (AFP) and sox17], (D) mesoderm (desmin), and (E and F) ectoderm (Tuj-1 positive motor neurons) lineages. (F) Represents the enlarged view of the boxed area in (E). (Scale bars, 100 μm.) (G-L) Upon injection into nude mice, hASC-iPS cells form (G) teratoma in vivo, which contains tissues of all three embryonic germ layers, such as (H) neural epithelium (ectoderm), (I) smooth muscle (arrow) and (J) adipose tissue (mesoderm), and (K) gut epithelium and (L) respiratory epithelium (endoderm).
Figure 20:
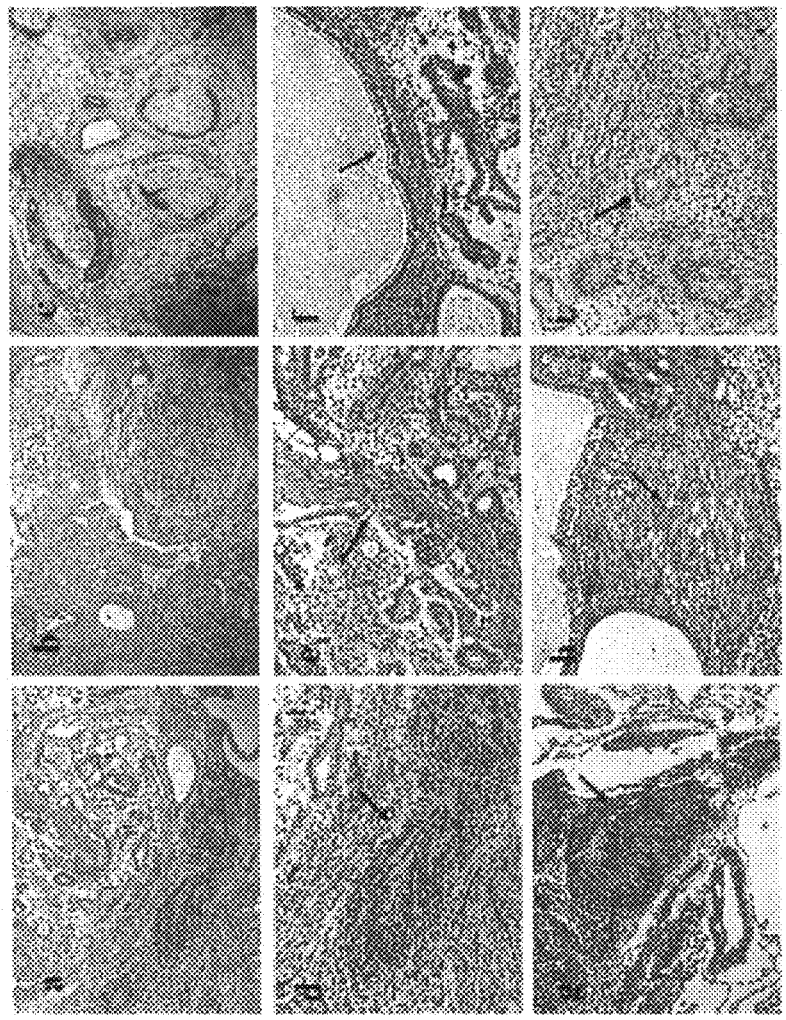
FIG. 20. Teratomas containing cells from three germ layers developed from iPS cell lines injected into the dorsal flank of nude mice. (a-c) Representative images of three teratomas developed from three different feeder-free derived hASC-iPS cell lines. (d and g) Neuroectoderm (arrows). (e and h) Muscle tissue (mesoderm) (arrows). (f) Gut epithelium (endoderm) (arrow). (i) Respiratory epithelium (endoderm) (arrow).

To further compare hASCs, hASC-iPS cells, and hES cells, whole genome expression profiling by microarray analysis was performed. hASC-iPS cells showed a high degree of similarity in their gene expression patterns and close Pearson correlation values with those of human ES cells, and were distinct from hASCs (FIG. 11D). To demonstrate pluripotency of our hASC-iPS cells, we performed both in vitro (EB formation) and in vivo (teratoma formation) differentiation assays. Two individual lines of hASC-iPS cells from two patients were tested, and each readily differentiated into derivatives of the three embryonic germ layers in vitro (FIG. 12 A-F). We also injected eight different lines of hASC-iPS cells from the four human patients (two lines from each individual) into the dorsal flanks of immunodeficient athymic mice. From all of the eight lines injected, teratoma-like masses containing tissues of all three embryonic germ layers were observed 7-8 weeks after injection (FIG. 12 G-L and FIG. 20).

Figure 13:
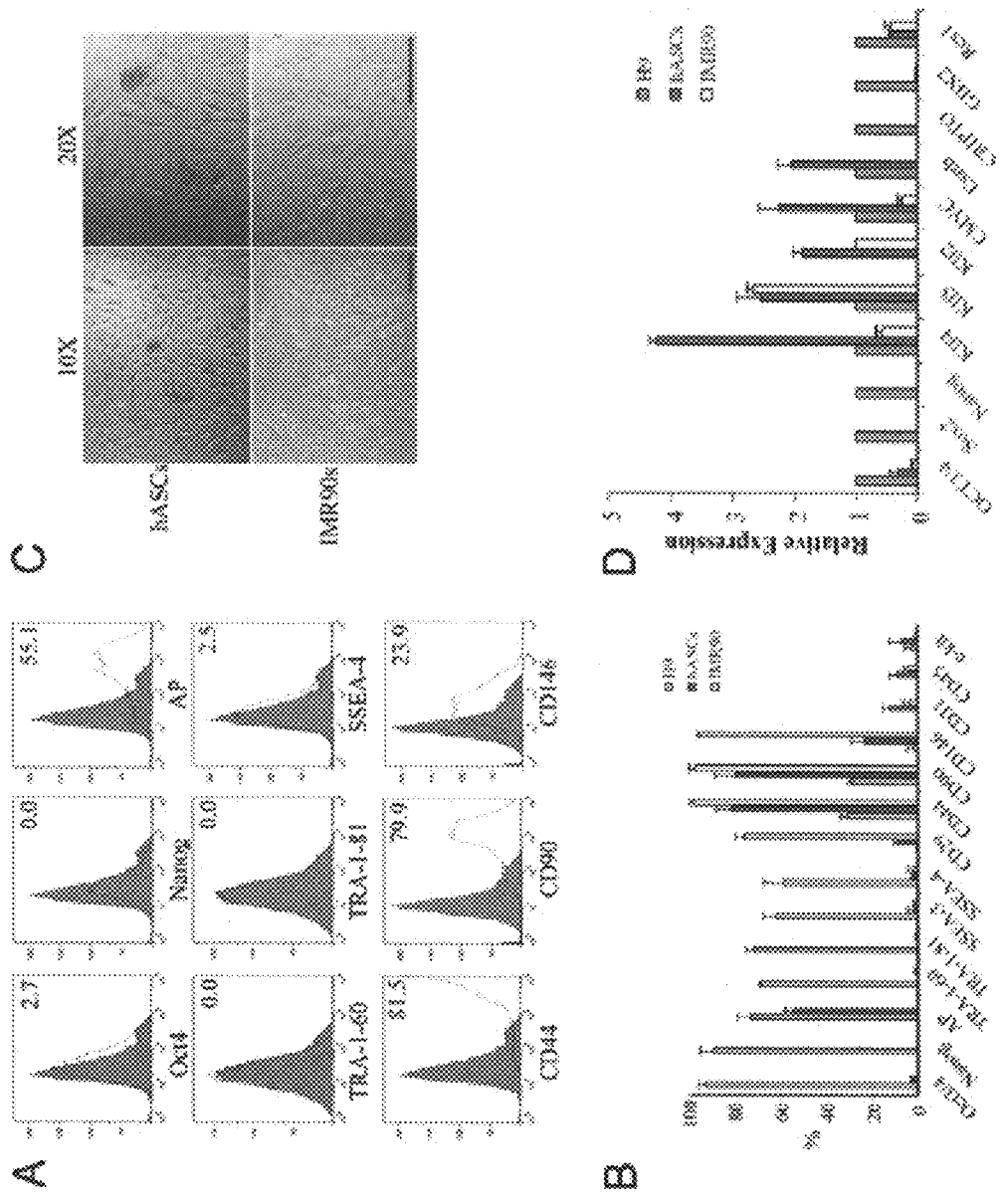
FIG. 13. Comparison of pluripotency and stem cell marker expression in hASCs with those in hES cells and IMR90 cells. (A) Representative histograms of FACS analysis showing hASCs expressed AP and mesenchymal stem cell markers CD44, CD90, and CD146 but not any of the pluripotency markers, such as Oct4, Nanog, TRA-1-60, TRA-1-81, and SSEA-4. Numbers indicate percent of positive cells that expressing each respective marker. (B). Quantitative analysis of cell markers expression in hASCs, H9 hES cells, and IMR90 cells by FACS. (C) AP staining of hASCs and IMR90s cultured in dish. Some hASCs express high AP activity (upper panels) while IMR90s (lower panels) did not. (Scale bars, 100 µm.) (D) Quantitative-PCR analysis of expressions level of pluripotency genes and reprogramming factors in hASCs and IMR90 cells relative to those in H9 hES cells. Note that Klf2 data were normalized to that of IMR90 cells.

To understand the factors that may contribute to the faster and more efficient reprogramming of hASCs relative to IMR90 human fibroblasts, we analyzed the expression of a list of pluripotency and surface markers in hASCs and compared with those of hES cells and IMR90s. Fluorescence-activated cell sorting (FACS) analysis indicated that ≈55% of hASCs (P0 cells) were positive for the early pluripotency marker AP (FIGS. 13A and B), which agreed with a previous report that a subpopulation of multipotent adipose derived stromal cells express AP. Staining the AP activity of in vitro cultured hASCs confirmed that some of the hASCs (heterogeneous in nature) expressed AP at various level (FIG. 13C). In contrast, IMR90 cells did not express any AP activity as indicated by FACS analysis and AP staining (FIGS. 13B and C). This result suggested that a subpopulation of multipotent hASCs already have unique stem cell properties that significantly different from the unipotent fibroblast cells.

Figure 21:
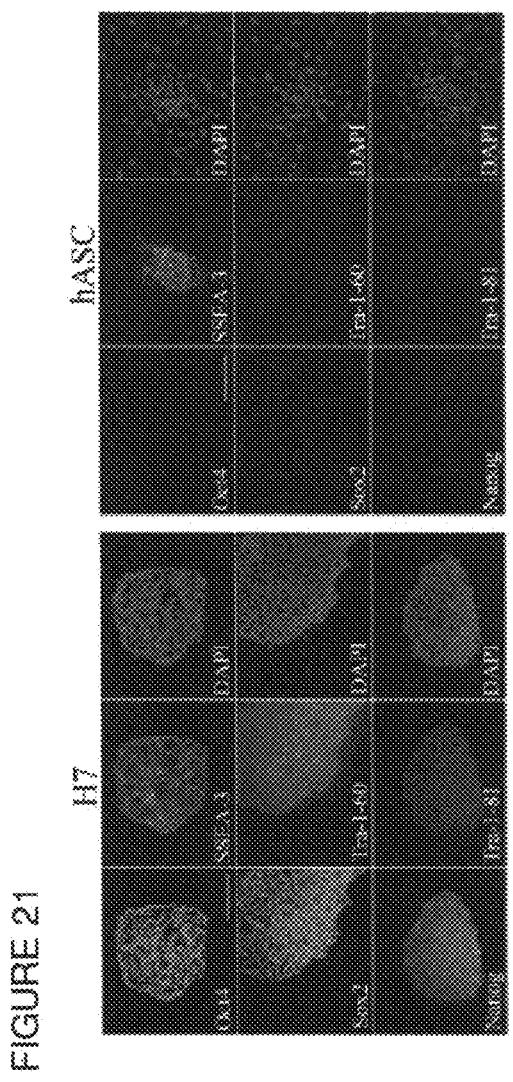
FIG. 21. Immunostaining of ES cell marker expression within H7 hES cells and within hASCs. Note that hASCs shown here formed the colony forming unit-fibroblast (CFU-F) in the center and expressed SSEA-3 within the CFU-F but not in surrounding individual cells. hASCs did not express other ES cell markers that were positive in H7 cells. (Scale bars, 100 µm.)

FACS analysis also indicated that individual hASCs expressed mesenchymal stem cell markers CD29, CD44, CD90, and CD146 (FIGS. 13A and B). hASCs did not express any of the pluripotency markers Oct4, Nanog, TRA-1-60, TRA-1-81, SSEA-3, and SSEA-4 (FIGS. 13A and B). Immunocytochemistry confirmed that individual hASCs did not express these pluripotency markers (FIG. 21). Interestingly, SSEA-3 was expressed when "colony-forming units-fibroblasts" (CFU-F) were formed (FIG. 21), but not in individual hASCs. We observed no pluripotency marker expression in IMR90 fibroblasts (FIG. 13B). Quantitative-PCR analysis of the expression level of certain pluripotency genes and reprogramming factors indicated that Klf4 (≈8-fold), Klf2 (≈2-fold), Esrrb (not detected in IMR90s), and c-MYC (≈9-fold) were expressed at a higher level in hASCs than those in IMR90s (FIG. 13D). Klf5 was expressed at a similar level in both hASCs and IMR90s, and was ≈2- to 3-fold higher than in hES cells (FIG. 13D). Klf4, Klf5, and Klf2 are the core Klf protein circuitry that regulates self-renewal of ES cells and Nanog expression. c-MYC itself is one of the reprogramming factors. Thus, these results overall indicated a clear difference at the gene expression level between hASCs and human fibroblasts.

We have generated human iPS cells from hASCs isolated from adult human patients (between the ages of 40-65) with a faster speed and higher efficiency than comparable studies targeting adult human fibroblasts using Yamanaka four factors. Furthermore, we show that human iPS cells can be readily generated under feeder-free conditions using adult hASCs, which reduces the variability of reprogramming associated with using mouse feeder cells. hASC-derived iPS cells express ES cell markers and genes associated with pluripotency at similar levels to hES cells and are morphologically indistinguishable from their hES cell counterparts. Hypomethylation patterns within the Oct4 and Nanog promoter regions and global mRNA expression patterns are also similar to hES cell profiles. hASC-derived iPS cells can differentiate into cell types belonging to all three germ layers both in vitro and in vivo, indicating they are true pluripotent cells.

As stated previously, hASCs are progenitor cells capable of differentiating into multiple lineages, including osteogenic, myogenic, and adipogenic fates. Because hASCs retain this plasticity with regard to differentiation, it is likely that these cells have an epigenomic regulatory pattern that is closer to pluripotent cells compared to terminally differentiated fibroblast cells. Thus, the unique epigenetic landscape of hASCs may present fewer barriers for reprogramming, resulting in higher efficiency and faster generation of iPS cells. Indeed, FACS analysis (FIGS. 13A and B) and AP staining (FIG. 13C) indicated that hASCs express AP activities, which is proposed as a most reliable early pluripotency marker of ES cells. Our results are consistent with a previous study showing that a subpopulation of $CD146^+$, $CD34^-$, $CD45^-$, $CD56^-$ cells isolated from human adipose tissue express strong AP activity and are multipotent. Thus, this unique property of hASCs clearly differs from the unipotent fibroblast cells without AP activity and may lead to higher efficiency of and faster reprogramming. Furthermore, quantitative-PCR (FIGS. 11B and 13D) and microarray (FIG. 11D) results show consistently high Klf4 expression within hASCs relative to not only fibroblasts, but also hES cells. Compared to IMR90 fibroblasts, hASCs also express higher level of pluripotency genes Klf2 and Esrrb, as well as the reprogramming factor c-MYC. hASCs also express Klf5 at a similar level with IMR90s. It is not a surprise to see relatively high Klf5 expression in IMR90s, because KLF5 has been shown to promote cell proliferation and present abundantly in epithelial cells. Klf4, Klf5, and Klf2 are the core KLF protein circuitry with redundant function in regulating self-renewal of ES cells and Nanog expression. Thus, the high endogenous expression level of Klf4, Klf2, Klf5, Esrrb, and c-MYC likely contributes toward the efficiency and speed by which hASCs can be reprogrammed.

Using hASCs as the parental cells for reprogramming has several advantages over other cell types such as neural stem cells, liver cells, and skin fibroblasts. First, the lipoaspiration procedure for isolating hASCs is relatively simple, fast, and safe. Second, it is easy to obtain a large quantity of hASCs as the starting population for reprogramming after a single lipoaspiration operation. Millions of hASCs can be derived on the same day of lipoaspiration, and the reprogramming can be performed immediately after the collected cells are seeded on culture dishes. In contrast, skin fibroblasts are typically derived from a small skin biopsy and require at least 4 weeks of culture and expansion to reach sufficient numbers for reprogramming. Third, unlike some cell types targeted for reprogramming, such as juvenile keratinocytes and neonatal fibroblasts, hASCs can be isolated from patients of all ages. This will have significant ramifications for clinical applications of iPS cells as it is more likely that older patients will require such therapies. In the future, these positive qualities of hASCs, combined with their faster reprogramming time as demonstrated in this study, could significantly reduce the time required for patients awaiting regenerative treatments.

Feeder-free derivation of iPS cells from hASCs thus represents a more clinically applicable method for derivation of iPS cells compared to other cell types and should enable more efficient and rapid generation of patient-specific and disease-specific iPS cells.

Materials and Methods

Cell Culture and Maintenance of hASC-iPS Cells. hASCs were maintained with Dulbecco's modified Eagle medium (DMEM) containing 10% FBS, Glutamax-I, 4.5 g/L glucose, 110 mg/L sodium pyruvate, 50 U/mL penicillin, and 50 µg/mL streptomycin at 37° C., 95% air, and 5% $CO_2$ in a humidified incubator. IMR90 human fibroblast cells were obtained from American Type Cell Culture (ATCC) and maintained with DMEM containing 10% FBS, L-glutamine, 4.5 g/L glucose, 100 U/mL penicillin, and 100 µg/mL streptomycin. All cells used for reprogramming were within passage two. Derived iPS cells were maintained either on MEF feeder layer or on Matrigel-coated tissue culture dishes (ES qualified; BD Biosciences) with mTESR-1 hES Growth Medium (Stemcell Technology).

Lentivirus Production and Transduction. 293FT cells (Invitrogen) were plated at ≈80% confluence per 100-mm dish and transfected with 12 µg each lentiviral vectors (Oct4, Sox2, Klf4, c-MYC) plus 8 µg packaging plasmids and 4 µg VSVG plasmids using Lipofectamine 2000 (Invitrogen) following the manufacturer's instructions. The resulting supernatant was collected 48 h after transfection, filtered through a 0.45-µm pore-size cellulose acetate filter (Whatman), and mixed with PEG-it Virus Concentration Solution (System Biosciences) overnight at 4° C. Viruses were precipitated at 1,500×g the next day and resuspended with Opi-MEM medium (Invitrogen).

Immunofluorescence and Alkaline Phosphatase Staining. Cells were fixed with 2% formaldehyde in PBS for 2 min, permeabilized with 0.5% Triton X-100 in PBS for 10 min, and blocked with 5% BSA in PBS for 1 h. Cells were then stained with appropriate primary antibodies and AlexaFluor-conjugated secondary antibodies (Invitrogen). The primary antibodies for Oct3/4 (Santa Cruz Biotechnology), Sox2 (Biolegend), Klf4 (Abcam), c-MYC (Abcam), SSEA-3 (Chemicon), SSEA-4 (Chemicon), Tra-1-60 (Chemicon), Tra-1-81 (Chemicon), Nanog (Santa Cruz Biotechnology), Desmin (Sigma), Sox17 (R&D System), and Tuj-1 (Covance) were used in the staining. Alkaline phosphatase (AP) staining was performed using the Quantitative Alkaline Phosphatase ES Characterization kit (Chemicon) following the manufacturer's instruction.

Quantitative-PCR. Total RNA and cDNA of each sample were prepared using the RNeasy Mini Plus kit (Qiagen) and the QuantiTect Reverse Transcription kit (Qiagen), respectively, following the manufacturer's instructions. Quantitative-PCR to measure mRNA expression levels was done with Taqman Gene Expression Assays (Applied Biosystems) using a SteponePlus Realtime-PCR System (Applied Biosystems) in the Protein and Nucleic Acid Facility at Stanford University School of Medicine.

In Vitro Differentiation. hASC-iPS cells cultured on Matrigel were treated with collagenase type IV (Invitrogen) and transferred to ultra-low attachment plates (Corning Life Sciences) in suspension culture for 8 days with DMEM/F12 (1:1) containing 20% knockout serum (Invitrogen), 4.5 g/L L-glutamine, 1% nonessential amino acids, 0.1 mM 2-mercaptoethanol, 50 U/mL penicillin, and 50 µg/mL streptomycin. EBs were then seeded in 0.25% gelatin-coated tissue culture dish for another 8 days. Spontaneous differentiation of hASC-iPS cells into cells of mesoderm and endoderm lineages was then detected with appropriate markers by immunofluorescence. Differentiation into dopaminergic neurons was carried out by co-culture of hASC-iPS cells with PA6 cells as previously described for hES cells.

Teratoma Formation. To form teratomas, ≈2 million hASC-iPS cells were harvested from Matrigel-coated culture dishes and injected s.c. to the dorsal flank of nude mice. After 6-8 weeks, tumors were dissected, and fixed with 10% formaldehyde in PBS. Parrafin embedded tissue sections were then generated and stained with hemotoxylin and eosin.

Bisulfite Pyrosequencing. Briefly, 1,000 ng sample DNA was bisulfate-treated using the Zymo DNA Methylation kit (Zymo Research). The PCR was then performed with one of the PCR primers biotinylated to convert the PCR product to single-stranded DNA templates. The PCR products were sequenced by Pyrosequencing PSQ96 HS System (Biotage) following the manufacturer's instructions (Biotage). The methylation status of each locus was analyzed individually as a T/C SNP using QCpG software (Biotage).

Microarray Hybridization and Data Acquisition. Total RNA samples were prepared using the RNeasy Mini Plus kit (Qiagen) from biological duplicate samples. Using Agilent Low RNA Input Fluorescent Linear Amplification kits, cDNA was reverse-transcribed, and cRNA then transcribed and fluorescently labeled with Cy5/Cy3. Cy3- and Cy5-labeled and amplified cRNA (825 ng) was hybridized to Agilent 4×44 K whole human genome microarrays (G4112F) and processed according to the manufacturer's instructions. The array was scanned using an Agilent G2505B DNA microarray scanner. The data were analyzed using GeneSpring GX 10.0 (Agilent Technologies) with multiple testing correction to identify genes that had statistically significant changes in expression between each group. For hierarchical clustering, we used Pearson correlation for similarity measure and for average linkage clustering.

Flow cytometry Analysis. FACS analysis of the hASCs (P0), H9 hES cells, and IMR90 cells were carried out using a BD LSR analyzer (BD Biosciences) at the Stanford Shared FACS Facility and data were analyzed by FlowJo (Tree Star). Antibodies used in this study were phycoerythrin (PE)-conjugated anti-CD29, CD31, SSEA-4, Oct3/4, Nanog, CD44, CD45, and c-Kit, FITC-conjugated CD90, and SSEA-3 (all from BD PharMingen). PE-anti-alkaline phosphatase, AlexaFluor488-conjugated TRA-1-60, and TRA-1-81 were obtained from Millipore. FITC-conjugated anti-CD146 was obtained from ABD Serotec. Dead cells stained by propidium-iodide were excluded from the analysis. Isotype-identical antibodies (BD PharMingen) were used as controls.

Derivation of hASCs. hASCs were obtained by lipoaspiration after acquiring informed consent from patients, in accordance with Stanford University human IRB guidelines. All suction assisted lipoaspiration procedures were performed using the VASER Lipo System (Sound Surgical Technologies). hASCs were harvested from the adipose tissue of male or female patients between the ages of 40 and 65 undergoing elective lipoaspiration. Participating patients had no prior knowledge or evidence of ongoing systemic disease at the time of operation. All specimens were immediately placed on ice and were washed sequentially in serial dilutions of dilute Betadine, followed by two PBS washes of equal volume. Adipose tissues were subsequently digested with an equal volume of 0.075% (wt/vol) Type II collagenase in Hank's balanced salt solution at 37° C. in water bath with agitation at 125 rpm for 30 min. After inactivation of collagenase with serum, the stromal vascular fraction was pelleted via centrifugation at 1,200×g for 5 min. The cell pellet was resuspended and filtered through a 100-μm cell strainer, and the collected cells were plated within 15-cm dishes for further expansion.

Figure 14:
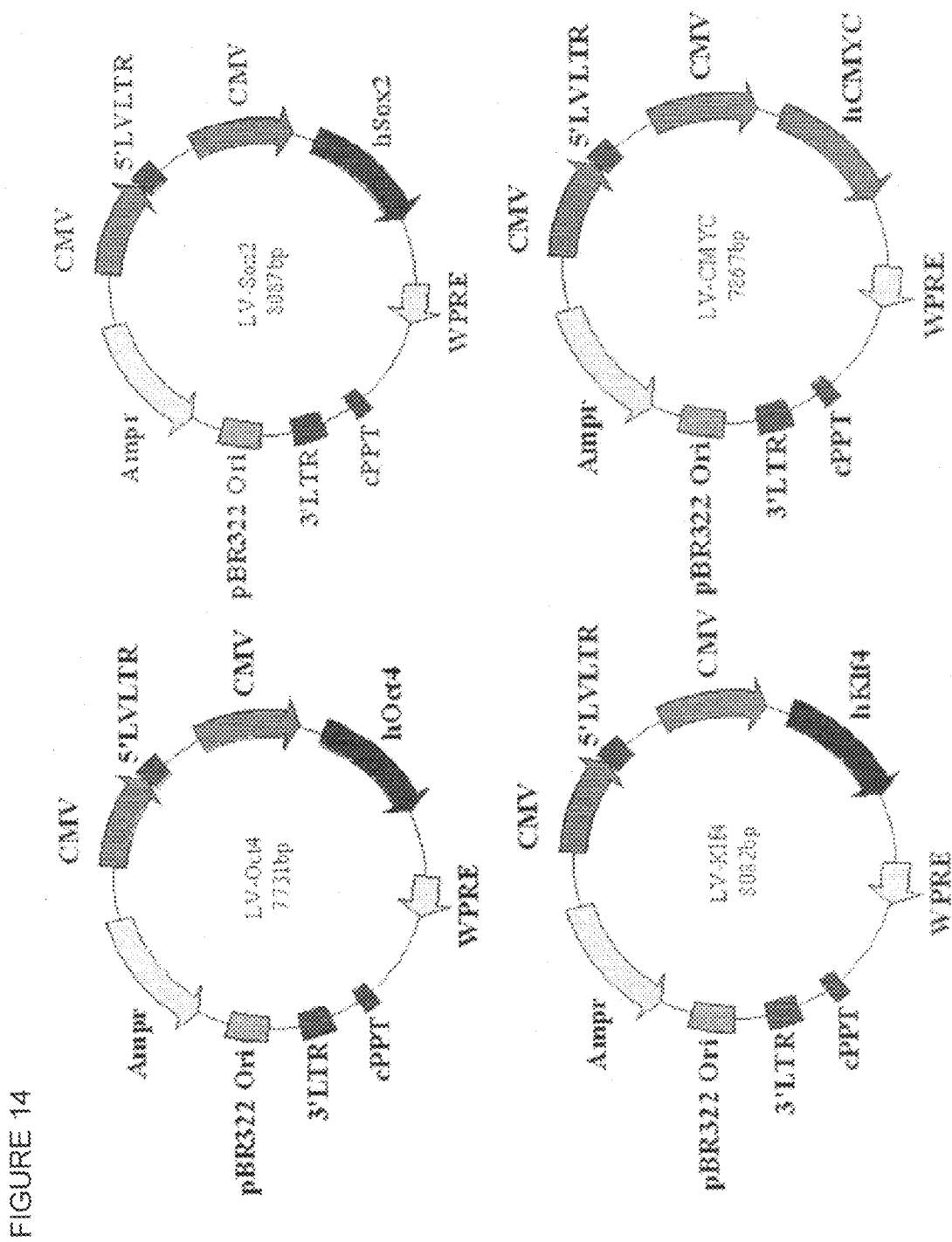
FIG. 14. Diagram showing the lentiviral constructs containing human Oct4, Sox2, Klf4, and c-MYC genes used for lentiviruses production. The pLL3.7 lentiviral plasmid was modified and used as the backbone for cloning human Oct4, Sox2, Klf4, or c-MYC driven under the CMV promoter.

Construction of Lentiviral Plasmids. Human Oct3/4, Sox2, Klf4, and c-MYC cDNAs were amplified by PCR using the high fidelity PfuUltra II fusion HS DNA polymerase (Agilent Technologies) and subcloned into modified pLL3.7 plasmids under the cytomegalovirus (CMV) promoter (FIG. 14). The sequence of each construct was confirmed as accurate by automated DNA sequencing at Geneway Incorporation. Protein expression of each factor was confirmed positive by western blotting analyses of transfected 293FT cells.

Reprogramming hASCs with Individual Lentiviruses. Reprogramming of hASCs was carried out either on MEF feeder cells or on Matrigel-coated feeder-free surfaces. For reprogramming on feeder cells, $2 \times 10^5$ hASCs were seeded in six-well tissue culture dish and maintained with hASC growth medium. The second day, cells were transduced with individual lentiviruses containing human Oct4, Sox2, Klf4, and c-MYC at a 1:1:1:1 ratio plus 5 μg/mL polybrene (Sigma). The day of this first time transduction was considered as day 0. Transduction was repeated on day 2 using the same batch of all four lentiviruses. On day 3, cells were digested off the culture dish with 0.05% trypsin-EDTA (Gibco) and counted with a hemocytometer. Cells (50,000) were then transferred onto mouse embryonic fibroblast (MEF) feeder layer in a gelatin-coated 10-cm culture dish and cultured with human embryonic stem (hES) cell growth medium mTeSR-1. The old medium was aspirated, and the cells were refreshed with new mTeSR-1 medium everyday. Background non-ES-like colonies usually appeared from day 5-6, while ES-like colonies with distinct light refractive property appeared as early as on day 12-13. On day 16-20, the living ES-like colonies were immunostained with TRA-1-60 mAb (Millipore) and Alexafluor488 secondary antibody (Invitrogen). Positive colonies with ES morphologies were picked out with a glass needle and seeded on Matrigel surface in a new culture dish. Each single picked colony was then maintained and expanded following routine ES cell passaging and culturing protocols and established as one individual hASC-iPS cell line. For feeder-free reprogramming, $2 \times 10^5$ hASCs were seeded in a well of six-well tissue culture dish previously coated with hES qualified matrigel (BD Biosciences). Cells were transduced twice with the four individual lentiviruses on day 0 and day 2. On day 4-5, the medium was switched from hASC growth medium to mTeSR-1. Cells were refreshed with mTeSR-1 everyday. ES-like colonies appeared as early as on day 13-14. On day 18-20, positive colonies with ES morphologies and TRA-1-60 expression were picked out and expanded in feeder-free condition.

Karyotype Analysis. Karyotype analyses of hASCs and hASC-iPS cells were carried out at the Cytogenetics Laboratory at Stanford Hospital and Clinics, Department of Pathology. Cells were treated with 0.1 mg/mL colcemid for induction of mitotic arrest and were subsequently harvested by trypsin dispersal, hypotonic shock, and fixation with 3:1 methanol:acetic acid. For each cell line, 20 metaphases were analyzed by the standard G-banding method.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A method of producing human iPS cells, comprising:
    contacting a population of human adipose stem cells with one or more minicircle DNA vectors encoding a plurality of reprogramming factors operably linked to a promoter; wherein the plurality of reprogramming factors comprises Oct4, Sox2, Lin28, and Nanog, or Oct4, Sox2, c-Myc, and Klf4; and
    maintaining the cells for a period of time sufficient to reprogram said human adipose stem cells to pluripotency in the absence of genomic integration of sequences of the one or more minicircle DNA vectors,
    wherein each of the one or more minicircle DNA vectors is 0.3-10 Kb in length, lacks an origin of replication, and lacks a drug selectable marker.

2. The method of claim 1, wherein a single minicircle DNA vector comprises the plurality of reprogramming factors sufficient to induce pluripotency of said somatic cells.

3. The method of claim 2, wherein the coding sequences of said reprogramming factors are all operably linked to the same single promoter.

4. The method of claim 3, wherein said coding sequences are separated sequences encoding self-cleaving peptides.

5. The method of claim 1, wherein said adipose stem cells are reprogrammed to pluripotency in feeder-layer free culture.

6. A method of producing human iPS cells, comprising:
(a) contacting a population of at least $1 \times 10^5$ human adipose stem cells with a minicircle DNA vector encoding a plurality of reprogramming factors, wherein the plurality of reprogramming factors comprises Oct4, Sox2, Lin28, and Nanog; or Oct4, Sox2, c-Myc, and Klf4, wherein (i) the coding sequences of the reprogramming factors are all operably linked to the same single promoter, and are separated from each other by a sequence encoding a self-cleaving 2A peptide sequence, and (ii) the minicircle DNA vector is 0.3-10 Kb in length, lacks an origin of replication, and lacks a drug selectable marker; and
(b) maintaining the cells in feeder-layer free culture on a matrigel coated surface for a period of time sufficient to reprogram said adipose stem cells to pluripotency in the absence of genomic integration of sequences of the minicircle DNA vector.

\* \* \* \* \*

SEQUENCE LISTING

<160> NUMBER OF SEQ ID NOS: 53

<210> SEQ ID NO 1
<211> LENGTH: 30
<212> TYPE: DNA
<213> ORGANISM: Artificial Sequence
<220> FEATURE:
<223> OTHER INFORMATION: Synthetic primer

<400> SEQUENCE: 1
gctgtcgaca tggcgggaca cctggcttcg                              30

<210> SEQ ID NO 2
<211> LENGTH: 30
<212> TYPE: DNA
<213> ORGANISM: Artificial Sequence
<220> FEATURE:
<223> OTHER INFORMATION: Synthetic primer

<400> SEQUENCE: 2
ctgtctagaa ccttccctcc aaccagttgc                              30

```
<210> SEQ ID NO 3
<211> LENGTH: 32
<212> TYPE: DNA
<213> ORGANISM: Artificial Sequence
<220> FEATURE:
<223> OTHER INFORMATION: Synthetic primer

<400> SEQUENCE: 3
gagggatcca tgtacaacat gatggagacg ga                                      32

<210> SEQ ID NO 4
<211> LENGTH: 76
<212> TYPE: DNA
<213> ORGANISM: Artificial Sequence
<220> FEATURE:
<223> OTHER INFORMATION: Synthetic primer

<400> SEQUENCE: 4
cagctcgaga gggccgggat tctcctccac gtcaccgcat gttagaagac ttcctctgcc        60
ctccatgtgt gagagg                                                        76

<210> SEQ ID NO 5
<211> LENGTH: 30
<212> TYPE: DNA
<213> ORGANISM: Artificial Sequence
<220> FEATURE:
<223> OTHER INFORMATION: Synthetic primer

<400> SEQUENCE: 5
cctgaattca tgagtgtgga tccagcttgt                                         30

<210> SEQ ID NO 6
<211> LENGTH: 78
<212> TYPE: DNA
<213> ORGANISM: Artificial Sequence
<220> FEATURE:
<223> OTHER INFORMATION: Synthetic primer

<400> SEQUENCE: 6
cagagatcta gggccgggat tctcctccac gtcaccgcat gttagaagac ttcctctgcc        60
ctctctcacg tcttcagg                                                      78

<210> SEQ ID NO 7
<211> LENGTH: 28
<212> TYPE: DNA
<213> ORGANISM: Artificial Sequence
<220> FEATURE:
<223> OTHER INFORMATION: Synthetic primer

<400> SEQUENCE: 7
caggctagct tcttctccga accaaccc                                           28

<210> SEQ ID NO 8
<211> LENGTH: 82
<212> TYPE: DNA
<213> ORGANISM: Artificial Sequence
<220> FEATURE:
<223> OTHER INFORMATION: Synthetic primer

<400> SEQUENCE: 8
aaggcggccg cagggccggg attctcctcc acgtcaccgc atgttagaag acttcctctg        60
ccctcaccgg tattctgtgc ct                                                 82

<210> SEQ ID NO 9
```

```
<211> LENGTH: 35
<212> TYPE: DNA
<213> ORGANISM: Artificial Sequence
<220> FEATURE:
<223> OTHER INFORMATION: Synthetic primer

<400> SEQUENCE: 9
gatgcggccg ccaccatggt gagcaagggc gagga                              35

<210> SEQ ID NO 10
<211> LENGTH: 77
<212> TYPE: DNA
<213> ORGANISM: Artificial Sequence
<220> FEATURE:
<223> OTHER INFORMATION: Synthetic primer

<400> SEQUENCE: 10
catgaattca gggccgggat tctcctccac gtcaccgcat gttagaagac ttcctctgcc   60
ctcggcgaag gcgatgg                                                  77

<210> SEQ ID NO 11
<211> LENGTH: 32
<212> TYPE: DNA
<213> ORGANISM: Artificial Sequence
<220> FEATURE:
<223> OTHER INFORMATION: Synthetic primer

<400> SEQUENCE: 11
catgtcgacg ttattaatag taatcaatta cg                                 32

<210> SEQ ID NO 12
<211> LENGTH: 41
<212> TYPE: DNA
<213> ORGANISM: Artificial Sequence
<220> FEATURE:
<223> OTHER INFORMATION: Synthetic primer

<400> SEQUENCE: 12
attgcggccg ctctcgagct tgggtctccc tatagtgagt c                       41

<210> SEQ ID NO 13
<211> LENGTH: 42
<212> TYPE: DNA
<213> ORGANISM: Artificial Sequence
<220> FEATURE:
<223> OTHER INFORMATION: Synthetic primer

<400> SEQUENCE: 13
tatgcggccg cgactagtga attcccgttg ttttgcaaat ga                      42

<210> SEQ ID NO 14
<211> LENGTH: 29
<212> TYPE: DNA
<213> ORGANISM: Artificial Sequence
<220> FEATURE:
<223> OTHER INFORMATION: Synthetic primer

<400> SEQUENCE: 14
tcatctagat acattgatga gtttggaca                                     29

<210> SEQ ID NO 15
<211> LENGTH: 17
<212> TYPE: DNA
<213> ORGANISM: Artificial Sequence
<220> FEATURE:
<223> OTHER INFORMATION: Synthetic primer
```

```
<400> SEQUENCE: 15 accccctggtg ccgtgaa                                                17

<210> SEQ ID NO 16
<211> LENGTH: 21
<212> TYPE: DNA
<213> ORGANISM: Artificial Sequence
<220> FEATURE:
<223> OTHER INFORMATION: Synthetic primer

<400> SEQUENCE: 16
ggctgaatac cttcccaaat a                                            21

<210> SEQ ID NO 17
<211> LENGTH: 18
<212> TYPE: DNA
<213> ORGANISM: Artificial Sequence
<220> FEATURE:
<223> OTHER INFORMATION: Synthetic primer

<400> SEQUENCE: 17
gcgatcaagc agcgacta                                                18

<210> SEQ ID NO 18
<211> LENGTH: 18
<212> TYPE: DNA
<213> ORGANISM: Artificial Sequence
<220> FEATURE:
<223> OTHER INFORMATION: Synthetic primer

<400> SEQUENCE: 18
ttcaccttcc ctccaacc                                                18

<210> SEQ ID NO 19
<211> LENGTH: 18
<212> TYPE: DNA
<213> ORGANISM: Artificial Sequence
<220> FEATURE:
<223> OTHER INFORMATION: Synthetic primer

<400> SEQUENCE: 19
cagcgcatgg acagttac                                                18

<210> SEQ ID NO 20
<211> LENGTH: 18
<212> TYPE: DNA
<213> ORGANISM: Artificial Sequence
<220> FEATURE:
<223> OTHER INFORMATION: Synthetic primer

<400> SEQUENCE: 20
ggagtgggag gaagaggt                                                18

<210> SEQ ID NO 21
<211> LENGTH: 19
<212> TYPE: DNA
<213> ORGANISM: Artificial Sequence
<220> FEATURE:
<223> OTHER INFORMATION: Synthetic primer

<400> SEQUENCE: 21
ccctgtggtt acctcttcc                                               19

<210> SEQ ID NO 22
```

```
<211> LENGTH: 18
<212> TYPE: DNA
<213> ORGANISM: Artificial Sequence
<220> FEATURE:
<223> OTHER INFORMATION: Synthetic primer

<400> SEQUENCE: 22
ctcccatttc cctcgttt                                                   18

<210> SEQ ID NO 23
<211> LENGTH: 18
<212> TYPE: DNA
<213> ORGANISM: Artificial Sequence
<220> FEATURE:
<223> OTHER INFORMATION: Synthetic primer

<400> SEQUENCE: 23
aaaggcaaac aacccact                                                   18

<210> SEQ ID NO 24
<211> LENGTH: 18
<212> TYPE: DNA
<213> ORGANISM: Artificial Sequence
<220> FEATURE:
<223> OTHER INFORMATION: Synthetic primer

<400> SEQUENCE: 24
gctattcttc ggccagtt                                                   18

<210> SEQ ID NO 25
<211> LENGTH: 18
<212> TYPE: DNA
<213> ORGANISM: Artificial Sequence
<220> FEATURE:
<223> OTHER INFORMATION: Synthetic primer

<400> SEQUENCE: 25
ctcctcccat ccctcata                                                   18

<210> SEQ ID NO 26
<211> LENGTH: 18
<212> TYPE: DNA
<213> ORGANISM: Artificial Sequence
<220> FEATURE:
<223> OTHER INFORMATION: Synthetic primer

<400> SEQUENCE: 26
aggctccaac catactcc                                                   18

<210> SEQ ID NO 27
<211> LENGTH: 18
<212> TYPE: DNA
<213> ORGANISM: Artificial Sequence
<220> FEATURE:
<223> OTHER INFORMATION: Synthetic primer

<400> SEQUENCE: 27
gttcggcttc ctgtccat                                                   18

<210> SEQ ID NO 28
<211> LENGTH: 18
<212> TYPE: DNA
<213> ORGANISM: Artificial Sequence
<220> FEATURE:
<223> OTHER INFORMATION: Synthetic primer

<400> SEQUENCE: 28
```

```
ctgcctcacc ctccttca                                                    18

<210> SEQ ID NO 29
<211> LENGTH: 18
<212> TYPE: DNA
<213> ORGANISM: Artificial Sequence
<220> FEATURE:
<223> OTHER INFORMATION: Synthetic primer

<400> SEQUENCE: 29
agccaagcca ctacattc                                                    18

<210> SEQ ID NO 30
<211> LENGTH: 18
<212> TYPE: DNA
<213> ORGANISM: Artificial Sequence
<220> FEATURE:
<223> OTHER INFORMATION: Synthetic primer

<400> SEQUENCE: 30
agatacgtca ttcgcaca                                                    18

<210> SEQ ID NO 31
<211> LENGTH: 22
<212> TYPE: DNA
<213> ORGANISM: Artificial Sequence
<220> FEATURE:
<223> OTHER INFORMATION: Synthetic primer

<400> SEQUENCE: 31
gcccctcatc agatccagat tt                                               22

<210> SEQ ID NO 32
<211> LENGTH: 20
<212> TYPE: DNA
<213> ORGANISM: Artificial Sequence
<220> FEATURE:
<223> OTHER INFORMATION: Synthetic primer

<400> SEQUENCE: 32
gcagctcaag gaagaggtgt                                                  20

<210> SEQ ID NO 33
<211> LENGTH: 20
<212> TYPE: DNA
<213> ORGANISM: Artificial Sequence
<220> FEATURE:
<223> OTHER INFORMATION: Synthetic primer

<400> SEQUENCE: 33
ggcgagctga gatttggata                                                  20

<210> SEQ ID NO 34
<211> LENGTH: 20
<212> TYPE: DNA
<213> ORGANISM: Artificial Sequence
<220> FEATURE:
<223> OTHER INFORMATION: Synthetic primer

<400> SEQUENCE: 34
ccagcctcca gagcctctat                                                  20

<210> SEQ ID NO 35
<211> LENGTH: 19
<212> TYPE: DNA
```

```
<213> ORGANISM: Artificial Sequence
<220> FEATURE:
<223> OTHER INFORMATION: Synthetic primer

<400> SEQUENCE: 35
attcgggcta aatggatgc                                                    19

<210> SEQ ID NO 36
<211> LENGTH: 20
<212> TYPE: DNA
<213> ORGANISM: Artificial Sequence
<220> FEATURE:
<223> OTHER INFORMATION: Synthetic primer

<400> SEQUENCE: 36
tagctccagg gtcttcatgg                                                   20

<210> SEQ ID NO 37
<211> LENGTH: 20
<212> TYPE: DNA
<213> ORGANISM: Artificial Sequence
<220> FEATURE:
<223> OTHER INFORMATION: Synthetic primer

<400> SEQUENCE: 37
tccttctacg gacggaactg                                                   20

<210> SEQ ID NO 38
<211> LENGTH: 20
<212> TYPE: DNA
<213> ORGANISM: Artificial Sequence
<220> FEATURE:
<223> OTHER INFORMATION: Synthetic primer

<400> SEQUENCE: 38
agaaatgcct gaggaaagca                                                   20

<210> SEQ ID NO 39
<211> LENGTH: 24
<212> TYPE: DNA
<213> ORGANISM: Artificial Sequence
<220> FEATURE:
<223> OTHER INFORMATION: Synthetic primer

<400> SEQUENCE: 39
ggaagaaatg ctgaaggtgg agac                                              24

<210> SEQ ID NO 40
<211> LENGTH: 22
<212> TYPE: DNA
<213> ORGANISM: Artificial Sequence
<220> FEATURE:
<223> OTHER INFORMATION: Synthetic primer

<400> SEQUENCE: 40
agtccccatc cccttcaata gc                                                22

<210> SEQ ID NO 41
<211> LENGTH: 20
<212> TYPE: DNA
<213> ORGANISM: Artificial Sequence
<220> FEATURE:
<223> OTHER INFORMATION: Synthetic primer

<400> SEQUENCE: 41
cacaactcgg agatcagcaa                                                   20
```

```
<210> SEQ ID NO 42
<211> LENGTH: 20
<212> TYPE: DNA
<213> ORGANISM: Artificial Sequence
<220> FEATURE:
<223> OTHER INFORMATION: Synthetic primer

<400> SEQUENCE: 42
ggtacttgta atccgggtgc                                            20

<210> SEQ ID NO 43
<211> LENGTH: 20
<212> TYPE: DNA
<213> ORGANISM: Artificial Sequence
<220> FEATURE:
<223> OTHER INFORMATION: Synthetic primer

<400> SEQUENCE: 43
gtccatcttt gcttgggaaa                                            20

<210> SEQ ID NO 44
<211> LENGTH: 20
<212> TYPE: DNA
<213> ORGANISM: Artificial Sequence
<220> FEATURE:
<223> OTHER INFORMATION: Synthetic primer

<400> SEQUENCE: 44
tagccaggtt gcgaagaact                                            20

<210> SEQ ID NO 45
<211> LENGTH: 20
<212> TYPE: DNA
<213> ORGANISM: Artificial Sequence
<220> FEATURE:
<223> OTHER INFORMATION: Synthetic primer

<400> SEQUENCE: 45
aattggtcca gccttggaat                                            20

<210> SEQ ID NO 46
<211> LENGTH: 18
<212> TYPE: DNA
<213> ORGANISM: Artificial Sequence
<220> FEATURE:
<223> OTHER INFORMATION: Synthetic primer

<400> SEQUENCE: 46
cgttgctcac agaccaca                                              18

<210> SEQ ID NO 47
<211> LENGTH: 20
<212> TYPE: DNA
<213> ORGANISM: Artificial Sequence
<220> FEATURE:
<223> OTHER INFORMATION: Synthetic primer

<400> SEQUENCE: 47
tgatcggaaa tgacactgga                                            20

<210> SEQ ID NO 48
<211> LENGTH: 20
<212> TYPE: DNA
<213> ORGANISM: Artificial Sequence
<220> FEATURE:
```

```
<223> OTHER INFORMATION: Synthetic primer

<400> SEQUENCE: 48
cacgactcca tgttggtcac                                              20

<210> SEQ ID NO 49
<211> LENGTH: 18
<212> TYPE: DNA
<213> ORGANISM: Artificial Sequence
<220> FEATURE:
<223> OTHER INFORMATION: Synthetic primer

<400> SEQUENCE: 49
ctctgcctcc tccacgaa                                                18

<210> SEQ ID NO 50
<211> LENGTH: 20
<212> TYPE: DNA
<213> ORGANISM: Artificial Sequence
<220> FEATURE:
<223> OTHER INFORMATION: Synthetic primer

<400> SEQUENCE: 50
cagaatccag acctgcacaa                                              20

<210> SEQ ID NO 51
<211> LENGTH: 18
<212> TYPE: DNA
<213> ORGANISM: Artificial Sequence
<220> FEATURE:
<223> OTHER INFORMATION: Synthetic primer

<400> SEQUENCE: 51
ggagcggtga agatggaa                                                18

<210> SEQ ID NO 52
<211> LENGTH: 20
<212> TYPE: DNA
<213> ORGANISM: Artificial Sequence
<220> FEATURE:
<223> OTHER INFORMATION: Synthetic primer

<400> SEQUENCE: 52
tacgtgttca tgccgttcat                                              20

<210> SEQ ID NO 53
<211> LENGTH: 16
<212> TYPE: PRT
<213> ORGANISM: D. melanogaster

<400> SEQUENCE: 53

Arg Gln Ile Lys Ile Trp Phe Gln Asn Arg Arg Met Lys Trp Lys Lys
 1               5                  10                  15
```